United States Patent
Peyman et al.

(10) Patent No.: US 6,743,800 B1
(45) Date of Patent: Jun. 1, 2004

(54) NAPHTHYRIDINE DERIVATIVES, PROCESSES FOR THEIR PREPARATION, THEIR USE AND PHARMACEUTICAL COMPOSITIONS COMPRISING THEM

(75) Inventors: Anuschirvan Peyman, Kelkheim (DE); Karl-Heinz Scheunemann, Liederbach (DE); Thomas R Gadek, Oakland, CA (US); Jean-Francois Gourvest, Claye Souilly (FR); Jean-Marie Ruxer, Issy les Moulineaux (FR)

(73) Assignees: Aventis Pharma Deutschland GmbH (DE); Genentech Inc.

( * ) Notice: Subject to any disclaimer, the term of this patent is extended or adjusted under 35 U.S.C. 154(b) by 0 days.

(21) Appl. No.: 10/030,301

(22) PCT Filed: Jun. 26, 2000

(86) PCT No.: PCT/EP00/05920

§ 371 (c)(1),
(2), (4) Date: Mar. 20, 2002

(87) PCT Pub. No.: WO01/02398

PCT Pub. Date: Jan. 11, 2001

(30) Foreign Application Priority Data

Jul. 2, 1999 (EP) ............................... 99112636

(51) Int. Cl.$^7$ ............ A61K 31/52; A61K 31/519; C07D 487/00; C07D 473/00; C07D 471/02

(52) U.S. Cl. ................ 514/263.22; 514/263.2; 514/265.1; 514/262.1; 514/303; 544/256; 544/264; 546/118

(58) Field of Search ........... 514/263.22, 263.2, 514/265.1, 262.1, 303; 544/256, 264; 546/118

(56) References Cited

U.S. PATENT DOCUMENTS 6,365,589 B1 * 4/2002 Gilligan et al. ............. 514/248
2003/0055059 A1 * 3/2003 Gilligan et al. ............. 514/243
2003/0216390 A1 * 11/2003 DeSimone et al. ......... 514/233.5

FOREIGN PATENT DOCUMENTS

| | | |
|---|---|---|
| EP | 0853084 | 7/1998 |
| WO | 9532710 | 12/1995 |
| WO | 9808940 | 3/1998 |
| WO | 0818461 | 5/1998 |
| WO | 9831359 | 7/1998 |
| WO | 9932457 | 7/1999 |
| WO | 9937621 | 7/1999 |

* cited by examiner

*Primary Examiner*—Russell Raymond
*Assistant Examiner*—Tamthom N. Truong
(74) *Attorney, Agent, or Firm*—Muserlian, Lucas and Mercanti

(57) ABSTRACT

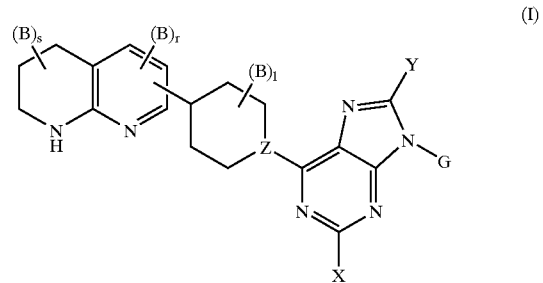

The present invention relates to compounds of formula (1), in which H, G, Z, X, Y, r, s and t have the meanings indicated in the claims, their physiologically tolerable salts and their prodrugs. The compounds of formula (1) are valuable, pharmacologically active compounds. They are vitronectin receptor antagonists and inhibitors of cell adhesion and are suitable for the therapy and prophylaxis of illnesses which are based on the interaction between vitronectin receptors and their ligands in cell-cell or cell-matrix interaction processes or which can be prevented, alleviated or cured by influencing such interactions. For example, they can be applied for inhibiting bone resorption by osteoclasts and thus for treating and preventing osteoporosis, or for inhibiting undesired angiogenesis or proliferation of cells of the vascular smooth musculature. The invention furthermore relates to processes for the preparation of compounds of formula (1), their use, in particular as active ingredients in pharmaceuticals, and pharmaceutical compositions comprising them.

9 Claims, No Drawings

NAPHTHYRIDINE DERIVATIVES, PROCESSES FOR THEIR PREPARATION, THEIR USE AND PHARMACEUTICAL COMPOSITIONS COMPRISING THEM

This application is a 371 of PCT/EP00/05920 filed Jun. 26, 2000.

The present invention relates to compounds of the formula I,

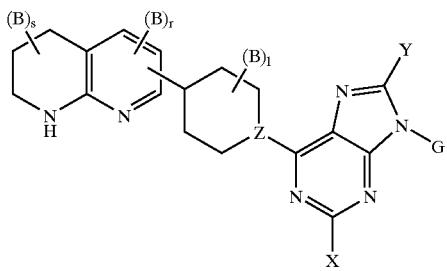

in which B, G, X, Y, Z, r, s and t have the meanings indicated below, their physiologically tolerable salts and their prodrugs. The compounds of the formula I are valuable pharmacologically active compounds. They are vitronectin receptor antagonists and inhibitors of cell adhesion and are suitable for the therapy and prophylaxis of illnesses which are based on the interaction between vitronectin receptors and their ligands in cell-cell or cell-matrix interaction processes or which can be prevented, alleviated or cured by influencing such interactions. For example, they can be applied for inhibiting bone resorption by osteoclasts and thus for treating and preventing osteoporosis, or for inhibiting undesired angiogenesis or proliferation of cells of the vascular smooth musculature. The invention furthermore relates to processes for the preparation of compounds of the formula I, their use, in particular as active ingredients in pharmaceuticals, and pharmaceutical compositions comprising them.

Human bones are subject to a constant dynamic renovation process comprising bone resorption and bone formation. These processes are controlled by types of cell specialized for these purposes. Bone resorption is based on the destruction of bone matrix by osteoclasts. The majority of bone disorders are based on a disturbed equilibrium between bone formation and bone resorption. Osteoporosis is a disease characterized by low bone mass and enhanced bone fragility resulting in an increased risk of fractures. It results from a deficit in new bone formation versus bone resorption during the ongoing remodelling process. Conventional osteoporosis treatment includes, for example, the administration of bisphosphonates, estrogens, estrogen/progesterone (hormone replacement therapy or HRT), estrogen agonists/antagonists (selective estrogen receptor modulators or SERMs), calcitonin, vitamin D analogues, parathyroid hormone, growth hormone secretagogues, or sodium fluoride (Jardine et al., Annual Reports in Medicinal Chemistry 31 (1996) 211).

Activated osteoclasts are polynuclear cells having a diameter of up to 400 μm, which remove bone matrix. Activated osteoclasts become attached to the surface of the bone matrix and secrete proteolytic enzymes and acids into the so-called "sealing zone", the region between their cell membrane and the bone matrix. The acidic environment and the proteases cause the destruction of the bone. The compounds of the formula I inhibit bone resorption by osteoclasts.

Studies have shown that the attachment of osteoclasts to the bones is controlled by integrin receptors on the cell surface of osteoclasts. Integrins are a superfamily of receptors which include, inter alia, the fibrinogen receptor $\alpha_{IIb}\beta_3$ on the blood platelets and the vitronectin receptor $\alpha_v\beta_3$. The vitronectin receptor $\alpha_v\beta_3$ is a membrane glycoprotein which is expressed on the cell surface of a number of cells such as endothelial cells, cells of the vascular smooth musculature, osteoclasts and tumor cells. The vitronectin receptor $\alpha_v\beta_3$, which is expressed on the osteoclast membrane, controls the process of attachment to the bones and bone resorption and thus contributes to osteoporosis. $\alpha_v\beta_3$ in this case binds to bone matrix proteins such as osteopontin, bone sialoprotein and thrombospontin which contain the tripeptide motif Arg-Gly-Asp (or RGD).

Horton and coworkers describe RGD peptides and an anti-vitronectin receptor antibody (23C6) which inhibit tooth destruction by osteoclasts and the migration of osteoclasts (Horton et al., Exp. Cell. Res. 195 (1991) 368). In J. Cell Biol. 111 (1990) 1713 Sato et al. describe echistatin, an RGD peptide from snake venom, as a potent inhibitor of bone resorption in a tissue culture and as an inhibitor of osteoclast adhesion to the bones. Fisher et al. (Endocrinology 132 (1993) 1411) and Yamamoto et al. (Endocrinology 139 (1998) 1411) were able to show in the rat that echistatin also inhibits bone resorption in vivo.

It was furthermore shown that the vitronectin $\alpha_v\beta_3$ on human cells of the vascular smooth musculature of the aorta stimulates the migration of these cells into the neointima which finally leads to arteriosclerosis and restenosis after angioplasty (Brown et al., Cardiovascular Res. 28 (1994) 1815). Yue et al. (Pharmacology Reviews and Communications 10 (1998) 9) show the inhibition of neointima formation using an $\alpha_v\beta_3$ antagonist.

Brooks et al. (Cell 79 (1994) 1157) showed that antibodies against $\alpha_v\beta_3$ or $\alpha_v\beta_3$ antagonists can cause a shrinkage of tumors by inducing the apoptosis of blood vessel cells during angiogenesis. The vitronectin receptor $\alpha_v\beta_3$ is also involved in the progression of a variety of other types of cancer, and is overexpressed in malignant melanoma cells (Engleman et al., Annual Reports in Medicinal Chemistry 31 (1996) 191). The melanoma invasiveness correlated with this overexpression (Stracke et al., Encylopedia of Cancer, volume III, 1855, Academic Press, 1997; Hillis et al., Clinical Science 91 (1996) 639). Carron et al. (Cancer Res. 58 (1998) 1930) describe the inhibition of tumor growth and the inhibition of hypercalcemia of malignancy using an $\alpha_v\beta_3$ antagonist.

Friedlander et al. (Science 270 (1995) 1500) describe anti-$\alpha_v\beta_3$ antibodies or $\alpha_v\beta_3$ antagonists which inhibit the bFGF-induced angiogenesis processes in the rat eye, a property which can be used therapeutically in the treatment of retinopathies and in the treatment of psoriasis. Storgard et al. (J. Clin. Invest. 103 (1999) 47) describe the use of $\alpha_v\beta_3$ antagonists in the treatment of arthritic diseases.

Influencing of the vitronectin receptor or of the interactions in which it is involved thus offers the possibility of influencing different disease states for whose therapy and prophylaxis there continues to be a need for suitable pharmaceutical active ingredients.

EP-A-528586 and EP-A-528587 disclose aminoalkyl-substituted or heterocyclyl-substituted phenylalanine derivatives, and WO-A-95/32710 discloses aryl derivatives as inhibitors of bone resorption by osteoclasts. In WO-A-95/28426 RGD peptides are described as inhibitors of bone resorption, angiogenesis and restenosis. International Patent Application PCT/EP98/08051 discloses carbamic ester derivatives, and International Patent Application PCT/EP99/00242 discloses sulfonamides which are vitronectin receptor antagonists. Further vitronectin receptor antagonists are disclosed in WO-A-98/08840 and WO-A-98/18461. Substituted purine derivatives as inhibitors of bone resorption are described in EP-A-853084. Further investigations have shown that the compounds of the formula I are particularly strong inhibitors of the vitronectin receptor and of bone resorption by osteoclasts.

The present invention relates to compounds of the formula I,

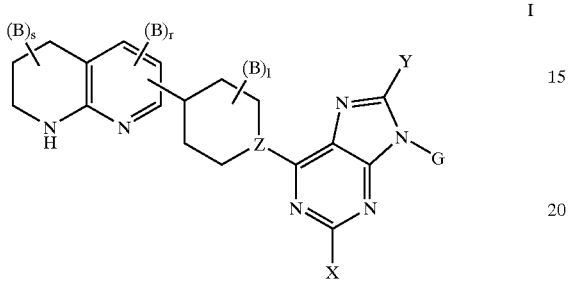

in which

G is a residue of the formula II

A is a direct bond, $-C(O)NR^5-$, $-NR^5(O)-$, $-C(O)-$, $-NR^5-$, $-O-$, $-S-$, $-S(O)-$, $-S(O)_2-$, $(C_2-C_4)$-alkynediyl, $(C_2-C_4)$-alkenediyl, $(C_5-C_{14})$-arylene where in the arylene residue one, two, three, four or five ring carbon atoms can be replaced by heteroatoms from the series consisting of nitrogen, oxygen and sulfur, or a divalent residue of a 3-membered to 7-membered saturated or unsaturated ring which can contain one or two ring heteroatoms from the series consisting of nitrogen, sulfur and oxygen and which can be monosubstituted or disubstituted by residues from the series consisting of $=O$, $=S$ and $R^3$;

B is $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, $(C_5-C_{14})$-heteroaryl, $(C_5-C_{14})$-heteroaryl-$(C_1-C_8)$-alkyl-, fluorine, chlorine, bromine, hydroxy, cyano, trifluoromethyl, nitro, hydroxycarbonyl-, $(C_1-C_6)$-alkoxy, $(C_1-C_6)$-alkoxy-$(C_1-C_6)$-alkyl-, $(C_1-C_6)$-alkoxycarbonyl-, $C_1-C_6$-alkylcarbonyl, $(C_5-C_{14})$-arylcarbonyl-, $(C_1-C_6)$-alkylaminocarbonyl-, $(C_1-C_6)$-alkoxy-$(C_1-C_6)$-alkoxy-, $(C_5-C_{14})$-aryl-$(C_1-C_8)$-alkylcarbonyl-, $(C_1-C_6)$-alkanoylamino-, $(C_1-C_6)$-alkylsulfonylamino-, $(C_5-C_{14})$-arylsulfonylamino-, $(C_1-C_6)$-alkylamino-, di-$((C_1-C_6)$-alkyl)amino-, $(C_1-C_6)$-alkylsulfonyl-, aminosulfonyl-, $(C_5-C_{14})$-arylsulfonyl-, $(C_5-C_{14})$-aryl-$(C_1-C_8)$-alkylsulfonyl-, $(C_5-C_{14})$-aryl or $(C_5-C_{14})$-heteroaryl, where all residues B are independent of one another and can be identical or different;

X is hydrogen, $NR^6R^{6+}$, fluorine, chlorine, bromine, $OR^6$, $SR^6$, hydroxy-$(C_1-C_6)$-alkyl-NH—, (hydroxy-$(C_1-C_6)$-alkyl)$_2$N—, amino-$(C_1-C_6)$-alkyl-NH—, (amino-$(C_1-C_6)$-alkyl)$_2$N—, hydroxy-$(C_1-C_6)$-alkyl-O—, hydroxy-$(C_1-C_6)$-alkyl-S— or —NH—C(O)—$R^6$;

Y is $R^6$, fluorine, chlorine, bromine, cyano, $NR^6R^{6+}$, $OR^6$, $SR^6$ or hydroxy-$(C_1-C_6)$-alkyl-NH—;

Z is N or CH:

$R^1$ and $R^2$ are hydrogen, fluorine, chlorine, cyano, nitro, $(C_1-C_{10})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, $(C_5-C_{14})$-heteroaryl, $(C_5-C_{14})$-heteroaryl-$(C_1-C_8)$-alkyl-, $R^6$—O—$R^7$, $R^6$—S(O)$_p$—$R^7$, $R^6S(O)_2NHR^7$, $R^6OC(O)NHR^7$ or $R^6R^{6+}N$—$R^7$, where all residues $R^1$ and $R^2$ are independent of one another and can be identical or different;

$R^3$ is hydrogen, fluorine, chlorine, cyano, nitro, $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, $(C_5-C_{14})$-heteroaryl, $(C_5-C_{14})$-heteroaryl-$(C_1-C_8)$-alkyl-, $R^6$—O—$R^7$, $R^6R^{6+}N$—$R^7$, $R^6C(O)$—O—$R^7$, $R^6C(O)R^7$, $R^6OC(O)R^7$, $R^6N(R^{6+})C(O)OR^7$, $R^6S(O)_pN(R^5)R^7$, $R^6OC(O)N(R^5)R^7$, $R^6C(O)N(R^5)R^7$, $R^6N(R^{6+})C(O)N(R^5)R^7$, $R^6N(R^{6+})S(O)_pN(R^5)R^7$, $R^6S(O)_pR^7$, $R^6SC(O)N(R^5)R^7$, $R^6N(R^{6+})C(O)R^7$ or $R^6N(R^{6+})S(O)_pR^7$ where alkyl can be mono-unsaturated or poly-unsaturated and where alkyl, cycloalkyl, aryl, and heteroaryl can be monosubstituted or polysubstituted by $R^6$, fluorine, chlorine, bromine, cyano, trifluoromethyl, $R^6R^{6+}NR^7$, nitro, $R^6OC(O)R^7$, $R^6C(O)R^7$, $R^6N(R^{6+})C(O)R^7$, $R^6N(R^{6+})S(O)_pR^7$ or $R^6$—O—$R^7$, and where all residues $R^3$ are independent of one another and can be identical or different;

$R^4$ is $-C(O)R^6$, $-C(S)R^8$, $-S(O)_pR^8$, $-P(O)R^8R^{8+}$ or a residue of a 4-membered to 8-membered saturated or unsaturated heterocycle which contains 1, 2, 3 or 4 heteroatoms from the series consisting of nitrogen, oxygen and sulfur;

$R^5$ is hydrogen, $(C_1-C_{10})$-alkyl, $(C_3-C_{14})$-cycloalkyl, $(C_3-C_{14})$-cycloalkyl-$(C_1-C_8)$-alkyl-, $(C_5-C_{14})$-aryl or $(C_5-C_{14})$-aryl-$(C_1-C_8)$-alkyl-, where all residues $R^5$ are independent of one another and can be identical or different;

$R^6$ and $R^{6+}$ are hydrogen, $(C_1-C_{18})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, $(C_5-C_{14})$-heteroaryl or $(C_5-C_{14})$-heteroaryl-$(C_1-C_8)$-alkyl- where aryl, heteroaryl, cycloalkyl and alkyl can be substituted one, two or three times by identical or different substituents from the series consisting of fluorine, chlorine, bromine, cyano, trifluoromethyl, nitro, hydroxycarbonyl-, $(C_1-C_6)$-alkyl, $(C_1-C_6)$-alkoxy, $(C_1-C_6)$-alkoxy-$(C_1-C_6)$-alkyl-, $(C_1-C_6)$-alkoxycarbonyl-, $(C_1-C_6)$-alkylcarbonyl-, $(C_1-C_6)$-alkylaminocarbonyl-, $(C_1-C_6)$-alkoxy-$(C_1-C_6)$-alkoxy-, $(C_5-C_{14})$-arylcarbonyl-, $(C_5-C_{14})$-aryl-$(C_1-C_8)$-alkylcarbonyl-, $(C_1-C_6)$-alkanoylamino-, $(C_5-C_{14})$-arylsulfonylamino-, $(C_1-C_6)$-alkylsulfonylamino-, $(C_1-C_6)$-alkylamino-, di-$((C_1-C_6)$-alkyl)amino-, $(C_1-C_6)$-alkylsulfonyl-, $(C_1-C_6)$-alkylaminosulfonyl-, $(C_5-C_{14})$-arylaminosulfonyl-, $(C_5-C_{14})$-aryl-$(C_1-C_8)$-alkylaminosulfonyl, $(C_5-C_{14})$-arylsulfonyl-, $(C_5-C_{14})$-aryl-$(C_1-C_8)$-alkylsulfonyl, $(C_5-C_{14})$-aryl and $(C_5-C_{14})$-heteroaryl, and where all residues $R^6$ and $R^{6+}$ are independent of one another and can be identical or different;

$R^7$ is $(C_1-C_4)$-alkanediyl or a direct bond, where all residues $R^7$ are independent of one another and can be identical or different;

$R^8$ and $R^{8+}$ are hydroxy, $(C_1-C_8)$-alkoxy, $(C_5-C_{14})$-aryl-$(C_1-C_8)$-alkoxy-, $(C_5-C_{14})$-aryloxy, $(C_1-C_8)$-alkylcarbonyloxy-$(C_1-C_4)$-alkoxy-, $(C_5-C_{14})$-aryl-$(C_1-C_8)$-alkylcarbonyloxy-$(C_1-C_8)$-alkoxy-, $NR^6R^{6+}$, (di-($(C_1-C_8)$-alkyl)amino)carbonylmethyloxy-, (di-($(C_5-C_{14})$-aryl-$(C_1-C_8)$-alkyl)amino)carbonylmethyloxy-, $(C_5-C_{14})$-arylamino-, the residue of an amino acid, N-($(C_1-C_4)$-alkyl)-piperidin-4-yloxy-, 2-methylsulfonylethoxy-, 1,3-thiazol-2-ylmethyloxy-, 3-pyridylmethyloxy-, 2-(di-($(C_1-C_4)$-alkyl)amino)-ethoxy or the residue $Q^-(CH_3)_3N^+$—$CH_2CH_2$—O— in which $Q^-$ is a physiologically tolerable anion, where all residues $R^8$ and $R^{8+}$ are independent of one another and can be identical or different;

n is zero, one, two, three, four or five;
m is zero, one, two, three, four or five,
i is zero or one;
q is zero, one or two;
r is zero, one or two;
s is zero, one, two or three;
t is zero, one, two, three, four, five, six, seven or eight;
p is zero, one or two, where all numbers p are independent of one another and can be identical or different;

in all their stereoisomeric forms and mixtures thereof in all ratios, and their physiologically tolerable salts and their prodrugs;

where, instead of the purine structure shown in formula I, also a 3-deazapurine structure, a 7-deazapurine structure or a 7-deaza-8-azapurine structure can be present.

All residues and numbers (or indices) which can occur several times in the compounds of the formula I, for example the residues B, $R^1$, $R^2$, $R^3$, $R^5$, $R^6$, $R^{6+}$, $R^7$ or the number p but also all other residues and numbers to which this applies, can each independently of one another have the meanings indicated. They can all be identical or different. Likewise, heteroatoms in heterocyclic rings or substituents in residues which can be present several times can in each case independently of one another have the meanings indicated and can all be identical or different.

Alkyl residues can be straight-chain or branched and can be saturated or mono-unsaturated or poly-unsaturated. This also applies if they carry substituents or occur as substituents on other residues, for example in alkoxy residues, alkoxycarbonyl residues or arylalkyl residues. Substituted alkyl residues can be substituted in any suitable position. Examples of alkyl residues containing from 1 to 18 carbon atoms are methyl, ethyl, propyl, butyl, pentyl, hexyl, heptyl, octyl, nonyl, decyl, undecyl, dodecyl, tetradecyl, hexadecyl and octadecyl, the n-isomers of all these residues, isopropyl, isobutyl, isopentyl, neopentyl, isohexyl, isodecyl, 3-methylpentyl, 2,3,4-trimethylhexyl, sec-butyl, tert-butyl, or tert-pentyl. A preferred group of alkyl residues is formed by the residues methyl, ethyl, n-propyl, isopropyl, n-butyl, isobutyl, sec-butyl and tert-butyl.

Unsaturated alkyl residues can contain one or more, for example one, two or three, double bonds and/or triple bonds. Of course, an unsaturated alkyl residue has to have at least two carbon atoms. Examples of unsaturated alkyl residues are alkenyl residues such as vinyl, 1-propenyl, allyl, butenyl or 3-methyl-2-butenyl, or alkynyl residues such as ethynyl, 1-propynyl or propargyl. Alkyl residues can also be unsaturated when they are substituted. Preferably an unsaturated alkyl residue is mono-unsaturated and contains one double bond or triple bond.

The above statements relating to alkyl residues correspondingly apply to divalent residues like alkanediyl residues, alkenediyl residues, alkynediyl residues, alkylene residues, alkenylene residues, alkynylene residues. Thus, alkanediyl residues, alkenediyl residues and alkynediyl residues can also be straight-chain or branched. The bonds via which the divalent residues are connected to their neighbouring groups can be located in any desired position. Examples of alkanediyl residues and alkylene residues are methylene (—$CH_2$—), methyl-methylene (1,1-ethanediyl) (—$C(CH_3)H$—), dimethyl-methylene(2,2-propanediyl)(—$C(CH_3)_2$—), 1,2-ethylene (—$CH_2$—$CH_2$), 1,3-propylene (—$CH_2$—$CH_2$—$CH_2$—) or 1,4-butylene (—$CH_2$—$CH_2$—$CH_2$—$CH_2$—). Examples of alkenylene residues are vinylene or propenylene, examples of alkynylene residues are ethynylene or propynylene.

Cycloalkyl residues can be monocyclic, bicyclic or tricyclic, i.e., they can be monocycloalkyl residues, bicycloalkyl residues and tricycloalkyl residues, provided they have a suitable number of carbon atoms and the parent hydrocarbons are stable. A bicylic or tricyclic cycloalkyl residue has to have at least 4 carbon atoms. Preferably a bicyclic or tricyclic cycloalkyl residue has at least 5 carbon atoms, more preferably at least 6 carbon atoms, and up to the number of carbon atoms specified in the respective definition. Thus, $(C_3-C_{14})$-cycloalkyl comprises but is not limited to, for example, $(C_3-C_{14})$-monocycloalkyl, $(C_6-C_{14})$-bicycloalkyl and $(C_6-C_{14})$-tricycloalkyl, and $(C_3-C_{12})$-cycloalkyl comprises but is not limited to, for example, $(C_3-C_{12})$-monocycloalkyl, $(C_6-C_{12})$-bicycloalkyl and $(C_6-C_{12})$-tricycloalkyl, Monocycloalkyl residues are, for example, cyclopropyl, cyclobutyl, cyclopentyl, cyclohexyl, cycloheptyl, cyclooctyl, cyclononyl, cyclodecyl, cycloundecyl, cyclododecyl or cyclotetradecyl which can also be substituted by, for example, $(C_1-C_4)$-alkyl. Examples of substituted cycloalkyl residues which may be mentioned are 4-methylcyclohexyl and 2,3-dimethylcyclopentyl.

Bicycloalkyl residues and tricycloalkyl residues can likewise be unsubstituted or substituted in any desired suitable position, for example by one or more oxo groups and/or one or more identical or different $(C_1-C_4)$-alkyl groups, for example methyl or isopropyl groups, preferably methyl groups. The bond via which the bicyclic or the tricyclic residue is bonded can be located in any desired position in the molecule; the residue can thus be bonded via a bridgehead atom or an atom in a bridge. The bond via which the residue is bonded can also be located in any desired stereochemical position, for example in an exo-position or an endoposition.

Examples of parent structures of bicyclic ring systems are norbornane (=bicyclo[2.2.1]heptane), bicyclo[2.2.2]octane and bicyclo[3.2.1]octane. An example of a system substituted by an oxo group is camphor (=1,7,7-trimethyl-2-oxobicyclo[2.2.1]heptane). Examples of parent structures of tricyclic systems are twistane (=tricyclo[4.4.0.0$^{3.8}$]decane, adamantane (=tricyclo[3.3.1.1$^{3.7}$]decane), noradamantane (=tricyclo[3.3.1.0$^{3.7}$]nonane), tricyclo[2.2.1.0$^{2.6}$]heptane. tricyclo[5.3.2.0$^{4.9}$]dodecane, tricyclo[5.4.0.0$^{2.9}$]undecane or tricyclo[5.5.1.0$^{3.11}$]tridecane. A residue derived from adamantane can be 1-adamantyl or 2-adamantyl.

$(C_5-C_{14})$-Aryl includes heterocyclic $(C_5-C_{14})$-aryl residues (=$(C_5-C_{14})$-heteroaryl residues) in which one or more of the 5 to 14 ring carbon atoms are replaced by heteroatoms such as nitrogen, oxygen or sulfur, and carbocyclic $(C_6-C_{14})$-aryl residues. Examples of carbocyclic $(C_6-C_{14})$-aryl residues are phenyl, naphthyl such as 1-naphthyl or 2-naphthyl, biphenylyl such as 2-biphenylyl, 3-biphenylyl or 4-biphenylyl, anthryl or fluorenyl, where ($C_6$–$C_{12}$)-aryl residues, in particular 1-naphthyl, 2-naphthyl and phenyl, are preferred. If not stated otherwise, aryl residues, in particular phenyl residues, can be unsubstituted or substituted by one or more, preferably one, two or three, identical or different substituents. In particular substituted aryl residues can be substituted by identical or different residues from the series consisting of ($C_1$–$C_8$)-alkyl, in particular ($C_1$–$C_4$)-alkyl, ($C_1$–$C_8$)-alkoxy, in particular ($C_1$–$C_4$)-alkoxy, fluorine, chlorine and bromine, nitro, amino, ($C_1$–$C_4$)-alkylamino, di-(($C_1$–$C_4$)-alkyl)amino, trifluoromethyl, hydroxy, methylenedioxy, cyano, hydroxycarbonyl-, aminocarbonyl-, ($C_1$–$C_4$)-alkoxycarbonyl-, phenyl, phenoxy, benzyl, benzyloxy, tetrazolyl, ($R^9$O)$_2$P(O)— and ($R^9$O)P(O)—O— where $R^9$ is hydrogen, ($C_1$–$C_{10}$)-alkyl, ($C_6$–$C_{14}$)-aryl or ($C_6$–$C_{14}$)-aryl-($C_1$–$C_8$)-alkyl. In general, only up to two nitro groups can be present in the compounds of formula I, and similarly all other groups, substituents or heteroatoms mentioned in the definition of the compounds of formula I can only be present in the compounds of formula I in such positions and in such numbers and in such combinations that the resulting molecule is stable and does not exhibit characteristics that are not desired for the intended use.

In monosubstituted phenyl residues the substituent can be located in the 2-position, the 3-position or the 4-position, the 3-position and the 4-position being preferred. If phenyl is disubstituted, the substituents can be in 2,3-position, 2,4-position, 2,5-position, 2,6-position, 3,4-position or 3,5-position. Preferably in disubstituted phenyl residues the two substituents are arranged in 3,4-position relative to the linkage site. In trisubstituted phenyl residues, the substituents can be in 2,3,4-position, 2,3,5-position, 2,3,6-position, 2,4,5-position, 2,4,6-position or 3,4,5-position. Similarly, naphthyl residues and other aryl residues can be substituted in any desired position, for example a 1-naphthyl residue in the 2-, 3-, 4-, 5-, 6-, 7- and 8-position, a 2-naphthyl residue in the 1-, 3-, 4-, 5-, 6-, 7- and 8-position.

Beside carbocyclic systems, ($C_5$–$C_{14}$)-aryl groups can also be monocyclic or polycyclic, for example monocyclic, bicyclic or tricyclic, aromatic ring systems in which 1, 2, 3, 4 or 5 ring carbon atoms are replaced by heteroatoms, in particular by identical or different heteroatoms from the series consisting of nitrogen, oxygen and sulfur. Examples of heterocyclic ($C_5$–$C_{14}$)-aryl groups and ($C_5$–$C_{14}$)-heteroaryl groups are pyridyl like 2-pyridyl, 3-pyridyl and 4-pyridyl, pyrrolyl like 2-pyrrolyl and 3-pyrrolyl, furyl like 2-fury and 3-furyl, thienyl like 2-thienyl and 3-thienyl, imidazolyl, pyrazolyl, oxazolyl, isoxazolyl, thiazolyl, isothiazolyl, tetrazolyl, pyridazinyl, pyrazinyl, pyrimidinyl, indolyl, isoindolyl, indazolyl, phthalazinyl, quinolyl, isoquinolyl, quinoxalinyl, quinazolinyl, cinnolinyl, O-carbolinyl, or benzo-fused, cyclopenta-fused, cyclohexa-fused or cyclohepta-fused derivatives of these residues. The heterocyclic systems can be substituted in any suitable position by the substituents listed above with respect carbocyclic aryl systems.

In the series of these heteroaryl groups, monocyclic or bicyclic aromatic ring systems which have 1, 2 or 3 ring heteroatoms, in particular 1 or 2 ring heteroatoms, from the series consisting of nitrogen, oxygen and sulfur and which can be unsubstituted or substituted by 1, 2 or 3 substituents from the series consisting of ($C_1$–$C_6$)-alkyl, ($C_1$–$C_6$)-alkoxy, fluorine, chlorine, nitro, amino, trifluoromethyl, hydroxy, ($C_1$–$C_4$)-alkoxycarbonyl-, phenyl, phenoxy, benzyloxy and benzyl, are preferred. Particularly preferred here are monocyclic or bicyclic aromatic 5-membered to 10-membered ring systems having 1, 2 or 3 heteroatoms, in particular having 1 or 2 ring heteroatoms, from the series consisting of nitrogen, oxygen and sulfur which can be substituted by 1 to 2 substituents from the series consisting of ($C_1$–$C_4$)-alkyl, ($C_1$–$C_4$)-alkoxy, phenyl, phenoxy, benzyl and benzyloxy. More particularly preferred are 5-membered or 6-membered monocyclic heteroaryl groups and 9-membered or 10-membered bicyclic heteroaryl groups containing 1 or 2, in particular 1, ring heteroatom from the series consisting of nitrogen, oxygen and sulfur which are unsubstituted or substituted as described before.

The above statements relating to aryl residues correspondingly apply to divalent arylene residues including heteroarylene residues. Arylene residues can be bonded to their neighbouring groups via any desired suitable positions. If an arylene residue is derived from a benzene ring the residue can be 1,2-phenylene, 1,3-phenylene or 1,4-phenylene, the latter two residues being preferred and 1,4-phenylene being especially preferred. If an arylene or heteroarylene residue is derived from a pyridine ring the two bonds via which it is connected can be in 1,2-position, 1,3-position or 1,4-position with respect to each other and in any desired position with respect to the ring nitrogen atom. Thus, a pyridinediyl residue can be, for example, 2,3-pyridinediyl, 2,4-pyridinediyl, 2,5-pyridinediyl, 2,6-pyridinediyl or 3,5-pyridinediyl. The above statements relating to aryl residues also correspondingly apply to the aryl moiety in groups like, for example, aryl-alkyl-. Examples of aryl-alkyl- residues which can also carry in the aryl moiety the substituents listed above, are benzyl, 1-phenylethyl or 2-phenylethyl.

The tetrahydro[1,8]naphthyridine ring depicted in formula I can be bonded to the 4-position of the 6-membered ring containing the group Z via any of the three positions in the aromatic ring, i.e. it can be a 5,6,7,8-tetrahydro[1,8]naphthyridin-2-yl residue, a 5,6,7,8-tetrahydro[1,8]naphthyridin-3-yl residue or a 5,6,7,8-tetrahydro[1,8]naphthyridin-4-yl residue. Preferably it is a 5,6,7,8-tetrahydro[1,8]naphthyridin-2-yl residue or a 5,6,7,8-tetrahydro[1,8]naphthyridin-3-yl residue, particularly preferably a 5,6,7,8-tetrahydro[1,8]naphthyridin-2-yl residue.

Examples of saturated and unsaturated rings, in particular of 3-membered to 7-membered saturated or unsaturated rings which can contain one or two heteroatoms such as nitrogen, sulfur or oxygen and which can optionally be monosubstituted or disubstituted by residues from the series consisting of =O, =S and $R^3$, are cyclopropane, cyclobutane, cyclopentane, cyclohexane, cycloheptane, cyclopentene, cyclohexene, cycloheptene, tetrahydropyran, 1,4-dioxacyclohexane, morpholine, thiomorpholine, piperazine, piperidine, pyrrolidine, dihydroisoxazole, tetrahydroisoxazole, 1,3-dioxolane, 1,2-dithiolane, 2,3-dihydrofuran, 2,5-dihydrofuran, tetrahydrofuran, 2,3-dihydrothiophene, 2,5-dihydrothiophene, 2-imidazoline, 3-imidazoline, 4-imidazoline, 2-oxazoline, 3-oxazoline, 4-oxazoline, 2-thiazoline, 3-thiazoline, 4-thiazoline, thiazolidine, 2H-thiapyran, 2H-pyran, 4H-pyran.

The residue of an amino acid representing $R^8$ or $R^{8+}$ is obtained from the corresponding amino acid, as is customary in peptide chemistry, by formally removing a hydrogen atom from an amino group. This amino group is then linked in peptide fashion through an amide bond to the C(O) group in the group $R^8$—C(O)—, to the CS group in the group $R^8$—CS—, etc. The amino acid from which $R^8$ or $R^{8+}$ can be derived can be a natural or unnatural amino acid and can be present in any stereochemical form, for example in the D form, the L form or in the form of a mixture of stereoisomers, for example in the form of a racemate. Preferred amino acids are α-amino acids and β-amino acids, α-amino acids being particularly preferred. Suitable amino acids which may be mentioned include, but are not limited to, Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, tert-butylglycine (Tbg), neopentylglycine (Npg), cyclohexylglycine (Chg), cyclohexylalanine (Cha), 2-thienylalanine (Thia), 2,2-diphenylaminoacetic acid, 2-(p-tolyl)-2-phenylaminoacetic acid, 2-(p-chlorophenyl)aminoacetic acid (cf. Houben-Weyl, Methoden der organischen Chemie [Methods of Organic Chemistry], Volume 15/1 and 15/2, Georg Thieme Verlag, Stuttgart, 1974). Functional groups in amino acids can be present in protected form or can be derivatized. For example, a carboxylic acid group present in an amino acid can also be present in the form of an ester or amide such as, for example, methyl ester, ethyl ester, n-propyl ester, isopropyl ester, isobutyl ester, tert-butyl ester, benzyl ester, unsubstituted amide, methylamide, ethylamide, ω-amino-(C$_2$–C$_8$-alkylamide or semicarbazide. Examples of protective groups such as, for example, urethane protective groups, carboxyl protective groups and side-chain protective groups are Aloc, Pyoc, Fmoc, Tcboc, Z, Boc, Ddz, Bpoc, Adoc, Msc, Moc, Z(NO$_2$), Z(Hal$_n$), Bobz, Iboc, Adpoc, Mboc, Acm, tert-butyl, OBzl, ONbzl, OMbzl, Bzl, Mob, Pic, Trt.

Optically active carbon atoms present in the compounds of the formula I can independently of one another have R configuration or S configuration. The compounds of the formula I can be present in the form of pure enantiomers or pure diastereomers or in the form of mixtures of enantiomers, for example in the form of racemates, or of mixtures of diastereomers. The present invention relates to both pure enantiomers and mixtures of enantiomers as well as to pure diastereomers and mixtures of diastereomers. The invention comprises mixtures of two or of more than two stereoisomers of the formula I, and it comprises all ratios of stereoisomers in the mixtures. Compounds of the formula I containing respective structural units can also be present as E isomers or Z isomers (or trans isomers or cis isomers). The invention relates to both pure E isomers, pure Z isomers, pure cis isomers, pure trans isomers and to E/Z mixtures and cis/trans mixtures in all ratios. The invention also comprises all tautomeric forms of the compounds of the formula I. Diastereomers, including E/Z isomers, can be separated into the individual isomers, for example, by chromatography. Racemates can be separated into the two enantiomers by customary methods, for example, by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

Physiologically tolerable salts of the compounds of formula I are nontoxic salts that are physiologically acceptable, in particular pharmaceutically utilizable salts. Such salts of compounds of the formula I containing acidic groups, for example carboxyl, are, for example, alkali metal salts or alkaline earth metal salts such as, for example, sodium salts, potassium salts, magnesium salts and calcium salts, and also salts with physiologically tolerable quaternary ammonium ions and acid addition salts with ammonia and physiologically tolerable organic amines such as, for example, triethylamine, ethanolamine or tris-(2-hydroxyethyl)amine. Basic groups in the compounds of the formula I can form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds of the formula I which simultaneously contain a basic group and an acidic group, for example a carboxyl group in addition to basic nitrogen atoms, can be present as zwitterions (or betaines or inner salts) which are likewise included by the present invention.

The physiologically tolerable anion Q$^-$ which is contained in the compounds of the formula I in case $R^8$ or $R^{8+}$ is the 2-trimethylammonio-ethoxy- residue is, in particular, a monovalent anion or an eqivalent of a polyvalent anion of a nontoxic physiologically acceptable, in particular also pharmaceutically utilizable, inorganic or organic acid, for example the anion or an anion equivalent of one of the abovementioned acids suitable for the formation of acid addition salts. Q$^-$ can thus be, for example, one of the anions (or an anion equivalent) from the group comprising chloride, sulfate, phosphate, acetate, citrate, benzoate, maleate, fumarate, tartrate, methanesulfonate and p-toluenesulfonate.

Salts of compounds of the formula I can be obtained by customary methods known to those skilled in the art, for example by combining a compound of the formula I with an inorganic or organic acid or base in a solvent or diluent, or from other salts by cation exchange or anion exchange. A subject of the present invention are also all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts.

The present invention moreover includes all solvates of compounds of the formula I, for example hydrates or adducts with alcohols, and also derivatives of the compounds of the formula I like esters, prodrugs and other physiologically tolerable derivatives, as well as active metabolites of the compounds of the formula I. The invention relates in particular to prodrugs of the compounds of the formula I which can be converted into compounds of the formula I under physiological conditions. Suitable prodrugs for the compounds of the formula I, i.e. chemically modified derivatives of the compounds of the formula I having properties which are improved in a desired manner, are known to those skilled in the art. More detailed information relating to prodrugs and their preparation is found, for example, in Fleisher et al., Advanced Drug Delivery Reviews 19 (1996) 115; Design of Prodrugs, H. Bundgaard (ed.), Elsevier, 1985; or H. Bundgaard, Drugs of the Future 16 (1991)443; which are all incorporated herein by reference. Suitable prodrugs for the compounds of the formula I are especially ester prodrugs and amide prodrugs of carboxylic acid groups, in particular of a COOH group representing $R^4$, for example alkyl esters, and also acyl prodrugs and carbamate prodrugs of acylatable nitrogen-containing groups such as amino groups or the tetrahydronaphthyridine group. In the acyl prodrugs or carbamate prodrugs, one or more, for example one or two, hydrogen atoms on nitrogen atoms in such groups are replaced by an acyl group or a carbamate group. Suitable acyl groups and carbamate groups for the acyl prodrugs and carbamate prodrugs are, for example, the groups $R^{10}$—C(O)— and $R^{11}$O—C(O)—, in which $R^{10}$ is hydrogen, $(C_1-C_{18})$-alkyl, $(C_3-C_{14})$-cycloalkyl, $(C_3-C_{14})$-cycloalkyl-$(C_1-C_8)$-alkyl-, $C_5-C_{14})$-aryl in which 1 to 5 carbon atoms can be replaced by heteroatoms such as nitrogen, oxygen or sulfur, or $(C_5-C_{14})$-aryl-$(C_1-C_8)$-alkyl- in which 1 to 5 carbon atoms in the aryl moiety can be replaced by heteroatoms such as nitrogen, oxygen or sulfur, and in which $R^{11}$ has the meanings indicated for $R^{10}$ with the exception of hydrogen.

The present invention is furthermore not restricted to the compounds shown in formula I which contain an actual purine substructure but also includes those analogous compounds which instead of the purine substructure shown in formula I contain a 3-deazapurine substructure, 7-deazapurine substructure or 7-deaza-8-azapurine substructure, i.e. those compounds which instead of the actual purine ring system contain one of the ring systems of formula IIIa, formula IIIb or formula IIIc wherein the 6-membered ring which contains the group Z and to which the tetrahydronaphthyridine residue is bonded is symbolized by the circular arc attached to the group Z. All the above and following explanations relating to compounds of the

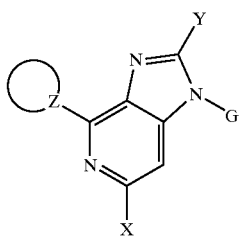

IIIa

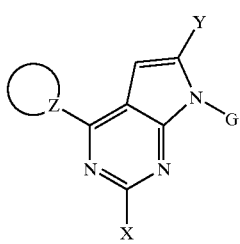

IIIb

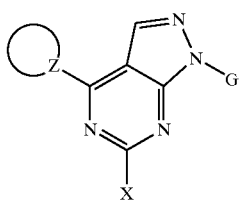

IIIa formula I correspondingly apply to these compounds. Unless stated otherwise, if compounds of the formula I are being discussed then the deaza analogs and deaza-aza analogs are also included. Preferably, in the compounds of the invention the actual purine structure shown in formula I is present, in which the nitrogen atoms in the 3-position and in the 7-position are actually present and a carbon atom to which the group Y is bonded is actually present in the 8-position.

The rings in the compounds of formula I which can carry substituents B, i.e. the aromatic ring and the non-aromatic ring in the tetrahydronaphthyridine moiety and the 6-membered ring containing the group Z, can independently of one another be unsubstituted or substituted where in substituted rings the substituents can be present in any desired position. If any of these rings is unsubstituted this means that the respective number r or s or t indicating the number of substituents B is zero. In such a case, i.e. if any of the rings is unsubstituted and the respective number r, s or t is zero, all positions on that ring which are not occupied by bonds connecting it to the neighbouring groups which are depicted in formula I, carry hydrogen atoms. If any of the rings is substituted this means that it carries one or more groups or atoms different from hydrogen from the group and atoms listed in the definition of B, and that the respective number r, s or t is different from zero. In such a case, i.e. if any of the rings is substituted and the respective number r, s or t is different from zero, all positions on that ring which are not occupied by substituents B or by bonds connecting it to neighbouring groups depicted in formula I carry hydrogen atoms. For example, the aromatic ring in the tetrahydronaphthyridine moiety has three positions to which neighbouring groups or substituents can be bonded. One of these positions is occupied by the bond connecting the ring to the 6-memberd ring containing the group Z. If r is zero or one or two then the remaining two positions in the aromatic ring carry two hydrogen atoms and no substituent B, or one hydrogen atom and one substituent B, or no hydrogen atom and two substituents B, respectively. The number r preferably is zero or one, more preferably zero. The number s preferably is zero, one or two, more preferably zero. The number t preferably is zero, one, two, three or four, more preferably zero, one or two, particularly preferably zero. In a preferred embodiment of the invention r, s and t simultaneously are zero, i.e. the aromatic ring and the non-aromatic ring in the tetrahydronaphthyridine moiety as well as the 6-membered ring containing the group Z do not carry any substituents B but all positions not occupied by bonds to neighbouring groups depicted in formula I carry hydrogen atoms. The compounds of this preferred embodiment of the invention can thus be represented by the formula Ia. In a particularly preferred embodiment of the invention the tetrahydronaphthyridine residue is a connected to the 6-membered ring containing the group Z via its 2-position leading to compounds of the formula Ib. In formulae Ia and Ib G, X, Y and Z have the meanings given above for formula I.

Ia

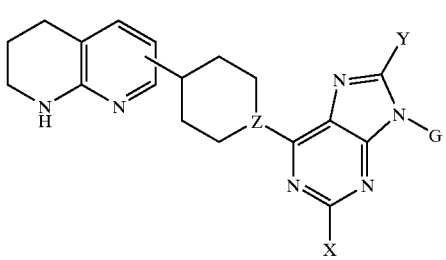

-continued

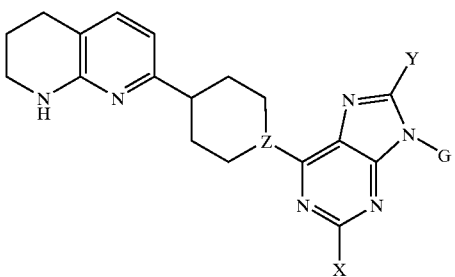

Ib

The number n preferably is zero, one or two, more preferably one.

The number m preferably is zero or one, more preferably zero.

The number i preferably is one.

The number q preferably is zero or one, more preferably zero.

Preferably in the compounds of formula I at least one of the numbers n, m, i and q is different from zero.

The group A preferably is a direct bond, i.e. the groups $(CR^1R^2)_n$ and $(CR^1R^2)_m$ are preferably bonded directly to one another.

The groups B preferably are independently of one another hydroxy or $(C_1-C_6)$-alkyl, more preferably hydroxy or $(C_1-C_4)$-alkyl.

The group X preferably is hydrogen, $NR^6R^{6+}$, hydroxy-$(C_1-C_6)$-alkyl- or $-NH-C(O)-R^6$, more preferably hydrogen, $NR^6R^{6+}$ or $-NH-C(O)-R^6$, particularly preferably hydrogen or $NH_2$, more particularly preferably hydrogen.

The group Y preferably is hydrogen.

The group Z preferably is N, i.e. a nitrogen atom.

The residues $R^1$ and $R^2$ preferably are independently of one another hydrogen or $(C_1-C_2)$-alkyl, more preferably hydrogen or methyl, particularly preferably hydrogen.

The residues $R^3$ preferably are independently of one another $R^6R^{6+}N-R^7$, $R^6OC(O)N(R^5)R^7$, $R^6S(O)_pN(R^5)R^7$, $R^6C(O)N(R^5)R^7$ or $R^6N(R^{6+})C(O)N(R^5)R^7$ where p here is 1 or 2 and preferably p here is 2. More preferably $R^3$ is $R^6OC(O)N(R^5)R^7$ or $R^6S(O)_pN(R^5)R^7$ where p here is 1 or 2 and preferably p here is 2. Particularly preferably $R^3$ is $R^6OC(O)N(R^5)R^7$ or $R^6S(O)_2N(R^5)R^7$. As stated above, in general the compounds of the present invention preferably exhibit a suitable degree of stability for the intended use. Therefore, in groups like $R^6OC(O)N(R^5)R^7$, $R^6S(O)_pN(R^5)R^7$ and $R^6S(O)_2N(R^5)R^7$ the residue $R^6$ preferably has one of the above meanings but does not denote hydrogen. In a preferred embodiment of the present invention the compounds of the formula I contain a lipophilic residue in the group $R^3$. A group of such preferred compounds is formed, for example, by those compounds in which $R^6$ and/or $R^{6+}$, for example in the group $R^6OC(O)N(R^5)R^7$ or $R^6S(O)_2N(R^5)R^7$, is $(C_4-C_{14})$-alkyl, $(C_5-C_{14})$-aryl-$(C_1-C_4)$-alkyl-, for example benzyl, $(C_5-C_{14})$-cycloalkyl or $(C_5-C_{14})$-cycloalkyl-$(C_1-C_4)$-alkyl-, preferred cycloalkyl residues here in particular being the 1-adamantyl residue and the 2-adamantyl residue, or is $(C_5-C_{14})$-aryl which is substituted with fluorine, chlorine or bromine, preferably chlorine, trifluoromethyl, $(C_1-C_6)$-alkyl or $(C_1-C_6)$-alkoxy.

$R^4$ preferably is $-C(O)-R^8$. The residue of a 4-membered to 8-membered heterocycle representing $R^4$ preferably is one of the residues tetrazolyl, imidazolyl, pyrazolyl, oxazolyl and thiadiazolyl.

The residues $R^5$ preferably are independently of one another hydrogen or $(C_1-C_4)$-alkyl, more preferably hydrogen or $(C_1-C_2)$-alkyl, particularly preferably hydrogen.

The residues $R^7$ preferably are independently of one another a direct bond or $(C_1-C_2)$-alkanediyl, more preferably a direct bond.

The residues $R^8$ and $R^{8+}$ preferably are independently of one another hydroxy or $(C_1-C_8)$-alkoxy, more preferably hydroxy or $(C_1-C_6)$-alkoxy, particularly preferably hydroxy or $(C_1-C_4)$-alkoxy.

Preferred compounds of the present invention are those compounds of the formula I in which one or more of the residues have preferred definitions, or have one or more specific denotations of the lists of denotations given in their respective definitions and in the general explanations on residues, all combinations of such preferred definitions and specific denotations being a subject of the present invention.

A group of preferred compounds is formed, for example, by compounds of the formula I in which G is a residue of the formula II

A is a direct bond, $-C(O)NR^5-$, $-NR^5C(O)-$, $-C(O)-$, $-NR^5-$, $-O-$, $-S-$, $-S(O)-$, $-S(O)_2-$, $(C_2-C_4)$-alkynediyl, $(C_2-C_4)$-alkenediyl, $(C_5-C_{14})$-arylene where in the arylene residue one, two, three, four or five ring carbon atoms can be replaced by heteroatoms selected from the series consisting of nitrogen, oxygen and sulfur, or a divalent residue of a 3-membered to 7-membered saturated or unsaturated ring which can contain one or two ring heteroatoms from the series consisting of nitrogen, sulfur and oxygen and which can be monosubstituted or disubstituted by residues from the series consisting of =O, =S and $R^3$;

B is $(C_1-C_{12})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, $(C_5-C_{14})$-heteroaryl, $(C_5-C_{14})$-heteroaryl-$(C_1-C_8)$-alkyl-, fluorine, chlorine, bromine, hydroxy, cyano, trifluoromethyl, nitro, hydroxycarbonyl-, $(C_1-C_6)$-alkoxy, $(C_1-C_6)$-alkoxy-$(C_1-C_6)$-alkyl-, $(C_1-C_6)$-alkylcarbonyl-, $(C_5-C_{14})$-arylcarbonyl-, $(C_5-C_{14})$-aryl-$(C_1-C_6)$-alkylcarbonyl-$(C_1-C_6)$-alkylaminocarbonyl-, $(C_1-C_6)$-alkanoylamino-, $(C_1-C_6)$-alkylsulfonylamino-, $(C_5-C_{14})$-arylsulfonylamino-, $(C_1-C_6)$-alkylamino-, di-$((C_1-C_6)$-alkyl)amino-, $(C_1-C_6)$-alkylsulfonyl-, $(C_5-C_{14})$-arylsulfonyl-, $(C_5-C_{14})$-aryl-$(C_1-C_8)$-alkylsulfonyl-, $(C_5-C_{14})$-aryl or $(C_5-C_{14})$-heteroaryl, where all residues B are independent of one another and can be identical or different;

X is hydrogen, $NH_2$, $-NH-C(O)-R^6$ or OH;

Y is hydrogen;

Z is N;

$R^1$ and $R^2$ independently of one another are hydrogen, fluorine, chlorine, cyano, nitro, $(C_1-C_{10})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, $(C_5-C_{14})$-heteroaryl, $(C_5-C_{14})$-heteroaryl-$(C_1-C_8)$-alkyl-, $R^6-O-R^7$, $R^6S(O)_2NHR^7$, $R^6OC(O)NHR^7$ or $R^6R^{6+}N-R^7$, where all residues $R^1$ and $R^2$ are independent of one another and can be identical or different;

$R^3$ is hydrogen, fluorine, chlorine, cyano, nitro, $(C_1-C_8)$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, $(C_5-C_{14})$-heteroaryl, $(C_5-C_{14})$-heteroaryl-$(C_1-C_8)$-alkyl-, $R^6-O-R^7$, $R^6R^{6+}N-R^7$, $R^6C(O)-O-R^7$, $R^6C(O)R^7$, $R^6OC(O)R^7$, $R^6N$ ($R^{6+}$)C(O)O$R^7$, $R^6$S(O)$_p$N($R^5$)$R^7$, $R^6$OC(O)N($R^5$)$R^7$, $R^6$C(O)N($R^5$)$R^7$, $R^6$N($R^{6+}$)C(O)N($R^5$)$R^7$, $R^6$N($R^{6+}$)S(O)$_p$N($R^5$)$R^7$, $R^6$S(O)$_p$$R^7$, $R^6$SC(O)N($R^5$)$R^7$, $R^6$N($R^{6+}$)C(O)$R^7$ or $R^6$N(R6+)S(O)$_p$$R^7$, where alkyl can be mono unsaturated or poly-unsaturated and where alkyl, cycloalkyl, aryl and heteroaryl can be monosubstituted or polysubstituted by $R^6$, fluorine, chlorine, bromine, cyano, trifluoromethyl, $R^6R^{6+}$N$R^7$, nitro, $R^6$OC(O)$R^7$, $R^6$C(O)$R^7$, $R^6$N($R^6$)C(O)$R^7$, $R^6$N($R^{6+}$)S(O)$_p$$R^7$ or $R^6$—O—$R^7$, and where all residues $R^3$ are independent of one another and can be identical or different;

$R^4$ is —C(O)$R^8$ or —P(O)$R^8R^{8+}$;

$R^5$ is hydrogen, $(C_1$–$C_{10})$-alkyl, $(C_3$—$C_{14})$-cycloalkyl, $(C_3$–$C_{14})$-cycloalkyl-$(C_1$–$C_8)$-alkyl- or $(C_5$–$C_{14})$-aryl-$(C_1$–$C_8)$-alkyl-, where all residues $R^5$ are independent of one another and can be identical or different;

$R^6$ and $R^{6+}$ are hydrogen, $(C_1$–$C_{12})$-alkyl, $(C_3$–$C_{14})$-cycloalkyl, $(C_3$–$C_{14})$-cycloalkyl-$(C_1$–$C_8)$-alkyl-, $(C_5$–$C_{14})$-aryl, $(C_5$–$C_{14})$-aryl-$(C_1$–$C_8)$-alkyl-, $(C_5$–$C_{14})$-heteroaryl or $(C_5$–$C_{14}$-heteroaryl-$(C_1$–$C_8)$-alkyl- where aryl, heteroaryl, cycloalkyl and alkyl can be substituted one, two or three times by identical or different substituents from the series consisting of fluorine, chlorine, bromine, cyano, trifluoromethyl, nitro, hydroxycarbonyl-, $(C_1$–$C_6)$-alkyl, $(C_1$–$C_6)$-alkoxy, $(C_1$–$C_6)$-alkoxy-$(C_1$–$C_6)$-alkyl-, $(C_5$–$C_{14})$-arylcarbonyl-, $(C_5$–$C_{14})$-aryl-$(C_1$–$C_6)$-alkylcarbonyl-, $(C_1$–$C_6)$-alkanoylamino-, $(C_5$–$C_{14})$-arylsulfonylamino-, $(C_1$–$C_6)$-alkylsulfonylamino, $(C_1$–$C_6)$-alkylamino, di-$((C_1$–$C_6)$-alkyl)amino-, $(C_1$–$C_6)$-alkylsulfonyl-, $(C_5$–$C_{14})$-aryl and $(C_5$–$C_{14})$-heteroaryl, and where all residues $R^6$ and $R^{6+}$ are independent of one another and can be identical or different;

$R^7$ is $(C_1$–$C_4)$-alkanediyl or a direct bond, where all residues $R^7$ are independent of one another and can be identical or different;

$R^8$ and $R^{8+}$ are hydroxy, $(C_1$–$C_8)$-alkoxy, $(C_5$–$C_{14})$-aryl-$(C_1$–$C_8)$-alkoxy-, $(C_1$–$C_8)$-alkylcarbonyloxy-$(C_1$–$C_4)$-alkoxy- or NR$^6R^{6+}$ where all residues $R^8$ and $R^{8+}$ are independent of one another and can be identical or different;

n is zero, one, two, three, four or five;

m is zero, one, two, three, four or five;

i is zero or one;

q is zero, one or two;

r is zero, one or two;

s is zero, one, two or three;

t is zero, one, two, three, four, five, six, seven or eight;

p is zero, one or two, where all numbers p are independent of one another and can be identical or different;

in all their stereoisomeric forms and mixtures thereof in all ratios, and their physiologically tolerable salts and their prodrugs;

where in this group of compounds the analogs of the compounds of formula I having a 3-deazapurine structure, a 7-deazapurine structure or a 7-deaza-8-azapurine structure are not included.

A group of more preferred compounds is formed, for example, by compounds of the formula I in which G is a residue of the formula II

$$—(CR^1R^2)_n—A—(CR^1R^2)_m—(CR^1R^3)_i—(CR^1R^2)_q—R^4 \qquad II$$

A is a direct bond, —C(O)N$R^5$—, —N$R^5$C(O)—, —C(O)—, —N$R^5$—, —O—, —S(O)$_2$—, $(C_2$–$C_4)$-alkynediyl, $(C_2$–$C_4)$-alkenediyl or $(C_5$–$C_{14})$-arylene where in the arylene residue one, two or three ring carbon atoms can be replaced by heteroatoms from the series consisting of nitrogen, oxygen and sulfur;

B is $(C_1$–$C_6)$-alkyl, $(C_3$–$C_{14})$-cycloalkyl, $(C_3$–$C_{14})$-cycloalkyl-$(C_1$–$C_4)$-alkyl-, $(C_5$–$C_{14})$-aryl $(C_5$–$C_{14})$-aryl-$(C_1$–$C_4)$-alkyl-, $(C_5$–$C_{14})$-heteroaryl, $(C_5$–$C_{14})$-heteroaryl-$(C_1$–$C_4)$-alkyl-, fluorine, chlorine, bromine, hydroxy, cyano, trifluoromethyl, hydroxycarbonyl-, $(C_1$–$C_6)$-alkoxy, $(C_1$–$C_6)$-alkylcarbonyl-, $(C_5$–$C_{14})$ arylcarbonyl-, $(C_1$–$C_6)$-alkanoylamino-, $(C_1$–$C_6)$-alkylamino-, di-$((C_1$–$C_6)$-alkyl)amino-, $(C_5$–$C_{14})$-aryl or $(C_5$–$C_{14})$-heteroaryl, where all residues B are independent of one another and can be identical or different;

X is hydrogen, $NH_2$ or —NH—C(O)—$R^6$;

Y is hydrogen;

Z is N;

$R^1$ and $R^2$ are hydrogen, fluorine, chlorine, cyano, $(C_1$–$C_4)$-alkyl, $(C_3$–$C_{14})$-cycloalkyl, $(C_3$–$C_{14})$-cycloalkyl-$(C_1$–$C_4)$-alkyl-, $(C_5$–$C_{14})$-aryl, $(C_5$–$C_{14})$-aryl-$(C_1$–$C_4)$-alkyl-, $(C_5$–$C_{14})$-heteroaryl, $(C_5$–$C_{14})$-heteroaryl-$(C_1$–$C_4)$-alkyl-, $R^6$S(O)$_2$NH$R^7$ or $R^6$OC(O)NH$R^7$, where all residues $R^1$ and R2 are independent of one another and can be identical or different;

$R^3$ is hydrogen, fluorine, chlorine, cyano, nitro, $(C_1$–$C_{18})$-alkyl, $(C_3$–$C_{14})$-cycloalkyl, $(C_3$–$C_{14})$-cycloalkyl-$(C_1$–$C_8)$-alkyl-, $(C_5$–$C_{14})$-aryl, $(C_5$–$C_{14})$-aryl-$(C_1$–$C_8)$-alkyl-, $(C_5$–$C_{14})$-heteroaryl, $(C_5$–$C_{14})$-heteroaryl-$(C_1$–$C_8)$-alkyl-, $R^6R^{6+}$N—$R^7$, $R^6$C(O)$R^7$, $R^6$N($R^{6+}$)C(O)O$R^7$, $R^6$S(O)$_p$N($R^5$)$R^7$, $R^6$OC(O)N($R^5$)$R^7$, $R^6$C(O)N($R^5$)$R^7$, $R^6$N($R^{6+}$)C(O)N($R^5$)$R^7$, $R^6$N($R^{6+}$)S(O)$_p$N($R^5$)$R^7$, $R^6$S(O)$_p$$R^7$, $R^6$N($R^{6+}$)C(O)$R^7$ or $R^6$N($R^{6+}$)S(O)$_p$$R^7$, where alkyl can be mono-unsaturated or poly-unsaturated and where alkyl, cycloalkyl, aryl and heteroaryl can be mono-substituted or polysubstituted by $R^6$, fluorine, chlorine, bromine, cyano, trifluoromethyl, $R^6R^{6+}$N$R^7$, $R^6$C(O)$R^7$, $R^6$N($R^{6+}$)C(O)$R^7$, $R^6$N($R^{6+}$)S(O)$_p$$R^7$ or $R^6$—O—$R^7$;

$R^4$ is —C(O)$R^8$;

$R^5$ is hydrogen or $(C_1$–$C_4)$-alkyl, where all residues $R^5$ are independent of one another and can be identical or different;

$R^6$ and $R^{6+}$ are hydrogen, $(C_1$–$C_{12})$-alkyl, $(C_3$–$C_{14})$-cycloalkyl, $(C_3$–$C_{14})$-cycloalkyl-$(C_1$–$C_8)$-alkyl-, $(C_5$–$C_{14})$-aryl, $(C_5$–$C_{14})$-aryl-$(C_1$–$C_8)$-alkyl-, $(C_5$–$C_{14})$-heteroaryl or $(C_5$–$C_{14})$-heteroaryl-$(C_1$–$C_6)$-alkyl- where aryl, heteroaryl, cycloalkyl and alkyl can be substituted one, two or three times by identical or different substituents from the series consisting of fluorine, chlorine, bromine, cyano, trifluoromethyl, $(C_1$–$C_6)$-alkyl, $(C_1$–$C_6)$-alkoxy, $(C_1$–$C_6)$-alkylamino-, di-$((C_1$–$C_6)$-alkyl)amino-, $(C_5$–$C_{14})$-aryl and $(C_5$–$C_{14})$-heteroaryl, and where all residues $R^6$ and $R^{6+}$ are independent of one another and can be identical or different;

$R^7$ is $(C_1$–$C_2)$-alkanediyl or a direct bond, where all residues $R^7$ are independent of one another and can be identical or different, $R^8$ is hydroxy or $(C_1$–$C_8)$-alkoxy;

n is zero, one, two, three, four or five;

m is zero or one;

i is zero or one;
q is zero or one;
r is zero, one or two;
s is zero, one or two:
t is zero, one, two, three or four;
p is zero, one or two, where all numbers p are independent of one another and can be identical or different;
in all their stereoisomeric forms and mixtures thereof in all ratios, and their physiologically tolerable salts and their prodrugs;
where in this group of compounds the analogs of the compounds of formula I having a 3-deazapurine structure, a 7-deazapurine structure or a 7deaza-8-azapurine structure are not included.

A group of particularly preferred compounds is formed, for example, by compounds of the formula I in which G is a residue of the formula II

A is a direct bond, —C(O)NR$^5$—, —NR$^5$C(O)—, —C(O)—, —NR$^5$— or (C$_5$–C$_{14}$)-arylene where in the arylene residue one or two ring carbon atoms can be replaced by heteroatoms from the series consisting of nitrogen, oxygen and sulfur;

B is (C$_1$–C$_6$)-alkyl, chlorine, hydroxy, cyano, trifluoromethyl, (C$_1$–C$_6$)-alkoxy, (C$_1$–C$_6$)-alkylcarbonyl-, (C$_1$–C$_6$)-alkanoylamino-, (C$_1$–C$_6$)-alkylamino- or di-((C$_1$–C$_6$)-alkyl)amino-, where all residues B are independent of one another and can be identical or different;

X is hydrogen:

Y is hydrogen:

Z is N;

R$^1$ and R$^2$ are hydrogen, (C$_1$–C$_4$)-alkyl, R$^6$S(O)$_2$NHR$^7$ or R$^6$OC(C)NHR$^7$, where all residues R$^1$ and R$^2$ are independent of one another and can be identical or different;

R$^3$ is hydrogen, (C$_1$–C$_{12}$)-alkyl, (C$_3$–C$_{14}$)-cycloalkyl, (C$_3$–C$_{14}$)-cycloalkyl-(C$_1$–C$_6$)-alkyl-, (C$_5$–C$_{14}$)-aryl, (C$_5$–C$_{14}$)-aryl-(C$_1$–C$_6$)-alkyl-, (C$_5$–C$_{14}$)-heteroaryl, (C$_5$–C$_{14}$)-heteroaryl-(C$_1$–C$_6$)-alkyl-, R$^6$R$^{6+}$N—R$^7$, R$^6$S(O)$_2$N(R$^5$)R$^7$, R$^6$OC(O)N(R$^5$)R$^7$ or R$^6$C(O)N(R$^5$)R$^7$, where alkyl can be mono-unsaturated or poly-unsaturated and where alkyl, cycloalkyl, aryl and heteroaryl can be monosubstituted or polysubstituted by R$^6$, fluorine, chlorine, trifluoromethyl, R$^6$C(O)R$^7$ or R$^6$—O—R$^7$;

R$^4$ is —C(O)R$^8$;

R$^5$ is hydrogen or (C$_1$–C$_4$)-alkyl, where all residues R$^5$ are independent of one another and can be identical or different;

R$^6$ and R$^{6+}$ are hydrogen, (C$_1$–C$_{12}$)-alkyl, (C$_3$–C$_{14}$)-cycloalkyl, (C$_3$–C$_{14}$)-cycloalkyl-(C$_1$–C$_6$)-alkyl-, (C$_5$–C$_{14}$)-aryl, (C$_5$–C$_{14}$)-aryl-(C$_1$–C$_8$)-alkyl-, (C$_5$–C$_{14}$)-heteroaryl or (C$_5$–C$_{14}$)-heteroaryl-(C$_1$–C$_8$)-alkyl- where aryl, heteroaryl, cycloalkyl and alkyl can be substituted one, two or three times by identical or different substituents from the series consisting of fluorine, chlorine, bromine, cyano, trifluoromethyl, (C$_1$–C$_6$)-alkyl, (C$_1$–C$_6$)-alkoxy, (C$_1$–C$_6$)-alkylamino-, di-((C$_1$–C$_6$)-alkyl)amino-, (C$_5$–C$_{14}$)-aryl and (C$_5$–C$_{14}$)-heteroaryl, and where all residues R$^6$ and R$^{6+}$ are independent of one another and can be identical or different;

R$^7$ is (C$_1$–C$_2$)-alkanediyl or a direct bond, where all residues R$^7$ are independent of one another and can be identical or different;

R$^8$ is hydroxy or (C$_1$–C$_6$)-alkoxy;

n is zero, one, two, three, four or five;
m is zero or one;
i is zero or one;
q is zero or one;
r is zero or one;
s is zero, one or two;
t is zero, one, two, three or four;
in all their stereoisomeric forms and mixtures thereof in all ratios, and their physiologically tolerable salts and their prodrugs;
where in this group of compounds the analogs of the compounds of formula I having a 3-deazapurine structure, a 7-deazapurine structure or a 7-deaza-8-azapurine structure are not included.

A group of more particularly preferred compounds is formed, for example, by compounds of the formula I in which G is a residue of the formula II

A is a direct bond;

B is (C$_1$–C$_6$)-alkyl or hydroxy, where all residues B are independent of one another and can be identical or different;

X is hydrogen;

Y is hydrogen;

Z is N;

R$^1$ and R$^2$ are hydrogen, (C$_1$–C$_4$)-alkyl, R$^6$S(O)$_2$NHR$^7$ or R$^6$OC(O)NHR$^7$, where all residues R$^1$ and R$^2$ are independent of one another and can be identical or different;

R$^3$ is hydrogen, (C$_1$–C$_{12}$)-alkyl, (C$_3$–C$_{14}$)-cycloalkyl, (C$_3$–C$_{14}$)-cycloalkyl-(C$_1$–C$_6$)-alkyl-, (C$_5$–C$_{14}$)-aryl, (C$_5$–C$_{14}$)-aryl-(C$_1$–C$_6$)-alkyl-, (C$_5$–C$_{14}$)-heteroaryl, (C$_5$–C$_{14}$)-heteroaryl-(C$_1$–C$_6$)-alkyl-, R$^6$R$^{6+}$N—R$^7$, R$^6$S(O)$_2$N(R$^5$)R$^7$, R$^6$OC(O)N(R$^5$)R$^7$ or R$^6$C(O)N(R$^5$)R$^7$, where alkyl can be mono-unsaturated or poly-unsaturated and where alkyl, cycloalkyl, aryl and heteroaryl can be monosubstituted or polysubstituted by R$^6$, fluorine, chlorine, trifluoromethyl, R$^6$O(O)R$^7$ or R$^6$—O—R$^7$;

R$^4$ is —C(O)R$^8$;

R$^5$ is hydrogen or (C$_1$–C$_4$)-alkyl;

R$^6$ and R$^{6+}$ are hydrogen, (C$_1$–C$_{12}$)-alkyl, (C$_3$–C$_{14}$)-cycloalkyl, (C$_3$–C$_{14}$)-cycloalkyl-(C$_1$–C$_6$)-alkyl-, (C$_5$–C$_{14}$)-aryl, (C$_5$–C$_{14}$)-aryl-(C$_1$–C$_8$)-alkyl-, (C$_5$–C$_{14}$)-heteroaryl or (C$_5$–C$_{14}$)-heteroaryl-(C$_1$–C$_8$)-alkyl- where aryl, heteroaryl, cycloalkyl and alkyl can be substituted one, two or three times by identical or different substituents from the series consisting of fluorine, chlorine, bromine, cyano, trifluoromethyl, (C$_1$–C$_6$)-alkyl, (C$_1$–C$_6$)-alkoxy, (C$_1$–C$_6$)-alkylamino-, di-((C$_1$–C$_6$)-alkyl)amino-, (C$_5$–C$_{14}$)-aryl and (C$_5$–C$_{14}$)-heteroaryl, and where all residues R$^6$ and R$^{6+}$ are independent of one another and can be identical or different;

R$^7$ is a direct bond;

R$^8$ is hydroxy or (C$_1$–C$_4$)-alkoxy;

n is zero, one or two;
m is zero or one;
i is zero or one;
q is zero or one, r is zero or one;
s is zero, one or two;
t is zero;
in all their stereoisomeric forms and mixtures thereof in all ratios, and their physiologically tolerable salts and their prodrugs;
where in this group of compounds the analogs of the compounds of formula I having a 3-deazapurine structure, a 7-deazapurine structure or a 7-deaza-8-azapurine structure are not included.

A group of especially preferred compounds is formed, for example, by compounds of the formula I in which G is a residue of the formula II

A is a direct bond;
X is hydrogen;
Y is hydrogen;
Z is N;
  $R^1$ and $R^2$ are hydrogen or $(C_1-C_2)$-alkyl, where all residues $R^1$ and $R^2$ are independent of one another and can be identical or different;
  $R^3$ is $R^6R^{6+}N—R^7$, $R^6S(O)_2N(R^5)R^7$, $R^6OC(O)N(R^5)R^7$ or $R^6C(O)N(R^5)R^7$;
  $R^4$ is —$C(O)R^8$;
    $R^5$ is hydrogen or $(C_1-C_2)$-alkyl;
    $R^6$ and $R^{6+}$ are hydrogen, $(C_1-C_{12})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_6)$-alkyl-, $(C_5-C_{14})$-heteroaryl or $(C_5-C_{14})$-heteroaryl-$(C_1-C_8)$-alkyl- where aryl, heteroaryl, cycloalkyl and alkyl can be substituted one, two or three times by identical or different substituents from the series consisting of fluorine, chlorine, bromine, cyano, trifluoromethyl, $(C_1-C_6)$-alkyl, $(C_1-C_6)$-alkoxy, $(C_1-C_6)$-alkylamino-, di-$((C_1-C_6)$-alkyl)amino-, $(C_5-C_{14})$-aryl and $(C_5-C_{14})$-heteroaryl, and where the residues $R^6$ and $R^{6+}$ are independent of one another and can be identical or different;
    $R^7$ is a direct bond;
    $R^8$ is hydroxy or $(C_1-C_4)$-alkoxy;
  n is zero, one or two;
  m is zero or one;
  i is zero or one;
  q is zero or one;
  r is zero;
  s is zero;
  t is zero;
in all their stereoisomeric forms and mixtures thereof in all ratios, and their physiologically tolerable salts and their prodrugs;
where in this group of compounds the analogs of the compounds of formula I having a 3-deazapurine structure, a 7-deazapurine structure or a 7-deaza-8-azapurine structure are not included.

A group of more especially preferred compounds is formed, for example, by compounds of the formula I in which G is a residue of the formula II

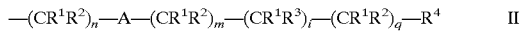

A is a direct bond;
X is hydrogen;
is hydrogen;
Z is N;
  $R^1$ and $R^2$ are hydrogen;
  $R^3$ is $R^6S(O)_2N(R^5)R^7$ or $R^6OC(O)N(R^5)R^7$;
  $R^4$ is —$C(O)R^8$;
    $R^5$ is hydrogen:
    $R^6$ is $(C_1-C_{12})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, $(C_5-C_{14})$-heteroaryl or $(C_5-C_{14})$-heteroaryl-$(C_1-C_8)$-alkyl- where aryl, heteroaryl, cycloalkyl and alkyl can be substituted one, two or three times by identical or different substituents from the series consisting of fluorine, chlorine, bromine, cyano, trifluoromethyl, $(C_1-C_6)$-alkyl, $(C_1-C_6)$-alkoxy, $(C_1-C_6)$-alkylamino-, di-$((C_1-C_6)$-alkyl)amino-, $(C_5-C_{14})$-aryl and $(C_5-C_{14})$-heteroaryl;
    $R^7$ is a direct bond;
    $R^8$ is hydroxy or $(C_1-C_4)$-alkoxy;
  n is one;
  m is zero;
  i is one;
  q is zero;
  r is zero;
  s is zero;
  t is zero;
in all their stereoisomeric forms and mixtures thereof in all ratios, and their physiologically tolerable salts and their prodrugs;
where in this group of compounds the analogs of the compounds of formula I having a 3-deazapurine structure, a 7-deazapurine structure or a 7-deaza-8-azapurine structure are not included.

Further, preferred compounds of the formula I are those in which, in case the number i is one, the residue $R^1$ in the group $(CR^1R^3)$ is hydrogen and the residue $R^3$ is an amino group or a substituted amino group, the chiral carbon atom carrying the residue $R^3$ has S configuration, and their physiologically tolerable salts and their prodrugs, where with respect to other stereoisomeric centers these compounds can be present in all their stereoisomeric forms and mixtures thereof in all ratios. Examples of residues $R^3$ that can be present in these preferred compounds of the formula I are the residues $R^6R^{6+}N—R^7$, $R^6S(O)_2N(R^5)R^7$, $R^6OC(O)N(R^5)R^7$ or $R^6C(O)N(R^5)R^7$ wherein $R^7$ is a direct bond. In particular in compounds of the formula I in which the numbers m and q are zero, the numbers i and n are one, A is a direct bond, $R^1$ and $R^2$ are hydrogen, $R^3$ is one of the residues $R^6R^{6+}N—R^7$, $R^6S(O)_2N(R^5)R^7$, $R^6OC(O)N(R^5)R^7$ or $R^6C(O)N(R^5)R^7$, and $R^7$ is a direct bond, i.e. for example in the compounds which form the above-defined group of more especially preferred compounds, the chiral carbon atom carrying the residue $R^3$ preferably has S configuration.

The present invention also relates to processes of preparation by which the compounds of the formula I are obtainable and which comprise carrying out one or more of the synthesis steps described below. The compounds of the formula I can generally be prepared, for example in the course of a convergent synthesis, by linkage of two or more fragments which can be derived retrosynthetically from the formula I. In the preparation of the compounds of the formula I it can generally be advantageous or necessary in the course of the synthesis to introduce functional groups which could lead to undesired reactions or side reactions in the respective synthesis step in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991). As examples of precursor groups nitro groups and cyano groups may be mentioned which can later be converted by reduction, for example by catalytic hydrogenation, into amino groups and aminomethyl groups, respectively. The protective groups exemplarily mentioned above with respect to functional groups in amino acid residues present in the compounds of formula I correspondingly can be used as protective groups for functional groups during the synthesis of the compounds of formula I.

For example, for the preparation of a compound of the formula I a building block of the formula IV

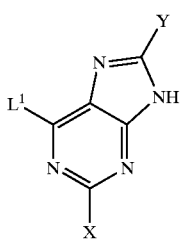

IV in which $L^1$ is a customary nucleophilically substitutable leaving group, can be used. Suitable groups $L^1$ are known to those skilled in the art and can be, for example chlorine, bromine, iodine, or a sulfonyloxy group like p-toluenesulfonyloxy (—OTos), methanesulfonyloxy (—OMes) or trifluoromethanesulfonyloxy (—OTf), preferably chlorine or bromine. X and Y in the compounds of formula IV are as defined above but functional groups can optionally also be present in the form of precursor groups or can be protected by customary protective groups. The compound of the formula IV is reacted with a building block of the formula V

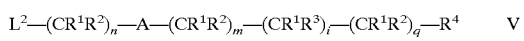

$$L^2-(CR^1R^2)_n-A-(CR^1R^2)_m-(CR^1R^3)_i-(CR^1R^2)_q-R^4 \quad V$$

wherein $R^1$, $R^2$, $R^3$, $R^4$, A, n, m, i and q are as defined above but wherein functional groups can optionally also be present in the form of precursor groups or can be protected by customary protective groups. In particular the group $R^4$ in a compound of the formula V can be a precursor group or a protected form of the final group $R^4$ that is to be present in the target compound of the formula I to be prepared. For example, a group $R^4$ is a compound of the formula I denoting hydroxycarbonyl-(—COOH) is preferably present in a compound of the formula V as a tert-butyl ester or a methyl ester or an ethyl ester group. The group $L^2$ in the compounds of formula V is hydroxy or a customary nucleophilically substitutable leaving group. Suitable leaving groups $L^2$ are known to those skilled in the art and can be, for example chlorine, bromine, iodine, —OTos, —OMes or —OTf. From the compounds of formulae IV and V a compound of formula VI

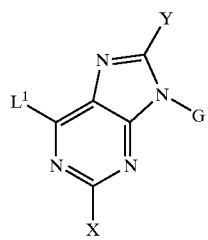

VI is obtained wherein G, X, Y and $L^1$ are as defined above but wherein functional groups can optionally also be present in the form of precursor groups or can be protected by customary protective groups. The reaction of the compounds of formula IV and V can be carried out according to methods known to those skilled in the art (see, for example, J. March, Advanced Organic Chemistry, Fourth Edition, Wiley, 1992, and source literature quoted therein). Preferably, the reaction is carried out in a suitable organic solvent or diluent, for example dichloromethane (DCM), chloroform, tetrahydrofuran (THF), diethyl ether, n-heptane, n-hexane, n-pentane, cyclohexane, diisopropyl ether, methyl tert-butyl ether, acetonitrile, dimethylformamide (DMF), dimethylsulfoxide (DMSO), dioxane, toluene, benzene, ethyl acetate or a mixture of these solvents, if appropriate with addition of a base such as, for example, butyllithium, lithium diisopropylamide (LDA), sodium hydride, sodium amide, potassium tert-butoxide, calcium carbonate, cesium carbonate, triethylamine, N,N-diisopropylethylamine or complex bases (for example sodium amide together with an alcoholate $R^{25}$ONa, where $R^{25}$ is ($C_2$-$C_6$)-alkyl or $CH_3CH_2OCH_2CH_2$—). With compounds of the formula V in which $L^2$ is hydroxy the reaction is carried out after activation of the hydroxy group, for example by reaction with triphenylphosphine and diethyl azodicarboxylate (DEAD) in THF under the conditions of the well-known Mitsunobu reaction.

For the preparation of a compound of the formula I in which Z is nitrogen a compound of the formula VI is then reacted with a compound of the formula VIIa,

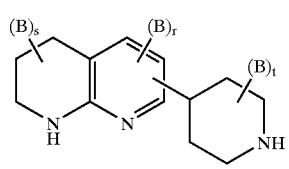

VIIa wherein B, r, s and t are defined as above but wherein functional groups can optionally also be present in the form of precursor groups or can be protected by customary protective groups. The reaction of the compounds of the formulae VI and VIIa can be carried out according to methods well-known to those skilled in the art (see, for example, J. March, Advanced Organic Chemistry, Fourth Edition, Wiley, 1992, and source literature quoted therein). In the reaction of a compound of the formula VI with a compound of the formula VIIa a nucleophilically substitutable leaving group in one reaction partner is replaced with a nucleophilic nitrogen atom in the other reaction partner as in the case of the reaction of the compounds of formulae IV and V. The above explanations on solvents or bases suitable for the reaction of the compounds of formula IV and V therefore correspondingly apply to the reaction of the compounds of formulae VI and VIIa. As a base in the reaction of the compounds of formulae VI and VIIa also an excess of the compound of formula VIIa can be used.

For the preparation of a compound of the formula I in which Z is CH a compound of the formula VI is reacted with a compound of the formula VIIb,

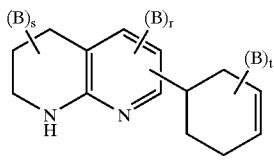

VIIb wherein B, r, s and t are defined as above but wherein functional groups can optionally also be present in the form of precursor groups or can be protected by customary protective groups. The reaction of the compounds of the formulae VI and VIIb can be carried out under the conditions of the Stille coupling as described, for example, in Langli et al., Tetrahedron 52 (1996) 5625 or Gundersen, Tetrahedron Lett. 35 (1994) 3153, or under the conditions of the Heck coupling as described, for example, in Koyama et al., Nucleic Acids Res., Symp. Ser. 11 (1982) 41 which are all incorporated herein by reference.

The reaction of a compound of the formula VI with a compound of the formula VIIa or VIIb, respectively, leads to a compound of the formula VIII,

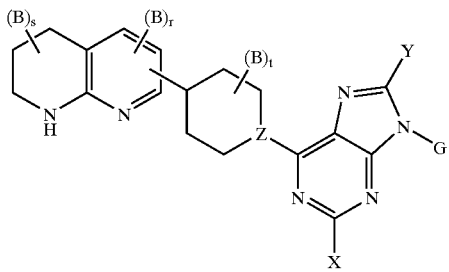

VIII wherein B, G, X, Y, Z, r, s and t are defined as above but wherein functional groups can optionally also be present in the form of precursor groups or can be protected by customary protective groups. Protective groups optionally still present in the compounds of the formula VII are then removed by standard processes. For example, tert-butyl ester groups, especially a tert-butyl ester group which represents the group $R^4$ in the group G in the compound of formula VIII and which is a protected form of hydroxycarbonyl group representing $R^4$ in the target compound of formula I, can be converted into the carboxylic acid groups by treatment with trifluoroacetic acid. Benzyl groups can be removed by hydrogenation. Fluorenylmethoxycarbonyl groups can be removed by secondary amines. If desired, further reactions can then be carried out by standard processes, for example acylation reactions or sulfonylation reactions of amino groups or esterification reactions. Further, for example, a substituent X in the 2-position of the purine structure can also be introduced at the end of the above-described synthesis of the compounds of formula I by known methods per se, for example as described in D. A. Nugiel, J. Org. Chem. 62 (1997) 201 or N. S. Gray, Tetrahedron Lett. 38 (1997) 1161 and the references quoted therein, and a substituent Y in the 8-position can be introduced by methods known per se as described, for example, in E. J. Reist et al., J. Org. Chem. 33 (1968) 1600; J. L. Kelley et al., J. Med. Chem. 33 (1990) 196 or E. Vanotti et al., Eur. J. Chem. 29 (1994) 287 which are all incorporated herein by reference. In addition, if desired a compound of the formula VIII or a compound obtained from a compound of the formula VIII can be converted into a physiologically tolerable salt or a prodrug by processes known per se to those skilled in the art.

In the synthesis of a compound of the formula I it is also possible first to react a compound of the formula IV with a compound of the formula VIIa or VIIb leading to replacement of the group $L^1$ in the formula IV by the naphthyridinyl-substituted 6-membered ring, and subsequently to react the resulting intermediate with a compound of the formula V.

The starting compounds of the formulae IV, V, VIIa and VIIb which are linked to give the compounds of the formula I, are commercially available or can be prepared by or analogously to processes described below or in the literature.

The compounds of the formula I are valuable pharmacologically active compounds which are suitable, for example, for the therapy and prophylaxis of bone disorders, tumor diseases, cardiovascular disorders or inflammatory conditions. The compounds of the formula I and their physiologically tolerable salts and their prodrugs can be administered to animals, preferably to mammals, and in particular to humans as pharmaceuticals for therapy or prophylaxis. They can be administered on their own or in mixtures with one another or in the form of pharmaceutical compositions or pharmaceutical preparations which permit enteral or parenteral administration and which, as active constituent, contain an efficacious dose of at least one compound of the formula I and/or its physiologically tolerable salts and/or its prodrugs in addition to customary pharmaceutically acceptable carrier substances and/or additives.

The present invention therefore also relates to the compounds of the formula I and/or their physiologically tolerable salts and/or their prodrugs for use as pharmaceuticals, to the use of the compounds of the formula I and/or their physiologically tolerable salts and/or their prodrugs for the production of pharmaceuticals for the therapy and prophylaxis of the diseases mentioned above or below, for example for the therapy and prophylaxis of bone disorders, and also to the use of the compounds of the formula I and/or their physiologically tolerable salts and/or their prodrugs for the therapy and prophylaxis of these diseases and to methods for such therapy and prophylaxis. The present invention furthermore relates to pharmaceutical compositions (or pharmaceutical preparations) which contain an efficacious dose of at least one compound of the formula I and/or its physiologically tolerable salts and/or its prodrugs and a customary pharmaceutically acceptable carrier.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions emulsions or tinctures, or in other ways, for example in the form of aerosols or nasal sprays.

The pharmaceutical compositions according to the invention are prepared in a manner known per se and familiar to those skilled in the art, one or more compound(s) of the formula I and/or its (their) physiologically tolerable salts and/or its (their) prodrugs being mixed with one or more pharmaceutically acceptable inert inorganic and/or organic carrier substances and/or additives and, if desired, one or more other pharmaceutically active compounds and being brought into a suitable administration form and dosage form that can be used in human or veterinary medicine. For the production of pills, tablets, coated tablets and hard gelatin capsules it is possible to use, for example, lactose, corn starch, or derivatives thereof, talc, stearic acid or its salts, etc. Carriers for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical compositions normally contain about 0.5 to 90% by weight of the compounds of the formula I and/or their physiologically tolerable salts and/or their prodrugs. The amount of the active ingredient of the formula I and/or its physiologically tolerable salts and/or its prodrugs in the pharmaceutical compositions normally is about 0.2 mg to about 500 mg, preferably about 1 mg to about 200 mg.

In addition to the active ingredients of the formula I and/or its physiologically tolerable salts and/or its prodrugs and carriers, the pharmaceutical compositions can contain additives (or auxiliary substances) such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I and/or their physiologically tolerable salts and/or their prodrugs. Furthermore, in addition to at least one compound of the formula I and/or its physiologically tolerable salts and/or its prodrugs, they can also contain one or more other therapeutically or prophylactically active ingredients.

The compounds of the formula I are antagonists of the vitronectin receptor and inhibitors of cell adhesion. They have, for example, the ability to inhibit the binding of osteoclasts to the bone surface and thereby inhibit bone resorption by osteociasts. The action of the compounds of the formula I can be demonstrated, for example, in an assay in which the inhibition of the binding of the isolated vitronectin receptor or of cells which contain the vitronectin receptor to a ligand of the vitronectin receptor is determined. Details of such an assay are given below. As vitronectin receptor antagonists, the compounds of the formula I and their physiologically tolerable salts and their prodrugs are generally suitable for the therapy and prophylaxis of diseases which are based on the interaction between vitronectin receptors and their ligands in cell-cell interaction processes or cell-matrix interaction processes, or which can be influenced by an inhibition of interactions of this type, or for the prevention, alleviation or cure of which an inhibition of interactions of this type is desired. As explained at the beginning, such interactions play a part, for example, in bone resorption, in angiogenesis or in the proliferation of cells of the vascular smooth musculature. The compounds of the formula I and their physiologically tolerable salts and their prodrugs are therefore suitable, for example, for the prevention, alleviation or cure of diseases which are caused at least partially by an undesired extent of bone resorption, angiogenesis or proliferation of cells of the vascular smooth musculature.

Bone diseases for whose treatment and prevention the compounds of the formula I according to the invention can be employed are especially osteoporosis, hypercalcemia, osteopenia, for example caused by metastases, dental disorders, hyperparathyroidism, periarticular erosions in rheumatoid arthritis and Paget's disease. In addition, the compounds of the formula I can be used for the alleviation, avoidance or therapy of bone disorders which are caused by a glucocorticoid, steroid or corticosteroid therapy or by a lack of sex hormone(s). All these disorders are characterized by bone loss which is based on the inequilibrium between bone formation and bone destruction and which can be favorably influenced by the inhibition of bone resorption by osteoclasts. The compounds of the formula I and/or their physiologically tolerable salts and/or their prodrugs can also favorably be used as inhibitor of bone resorption, for example in the therapy or prophylaxis of osteoporosis, in combination with conventional osteoporosis treatments, for example in combination with agents like bisphosphonates, estrogens, estrogen/progesterone, estrogen agonists/antagonists, calcitonin, vitamin D analogues, parathyroid hormone, growth hormone secretagogues, or sodium fluoride. Administration of the compounds of the formula I and/or their physiologically tolerable salts and/or their prodrugs and of other active ingredients effective in the treatment or prophylaxis of osteoporosis like those listed before can take place simultaneously or sequentially, in any order, and jointly or separately. For use in such a combination treatment or prophylaxis the compounds of the formula I and/or their physiologically tolerable salts and/or their prodrugs and one or more other active ingredients like those listed before can together be present in a single pharmaceutical composition, for example tablets, capsules or granules, or can be present in two or more separate pharmaceutical compositions which can be contained in a single package or in two or more separate packages. The use of the compounds of the formula I and/or their physiologically tolerable salts and/or their prodrugs in such a combination therapy or prophylaxis and their use in the production of pharmaceuticals for such a combination therapy or prophylaxis are also subjects of the present invention. The invention furthermore relates to pharmaceutical compositions which comprise efficacious amounts of at least one compound of the formula I and/or its physiologically tolerable salts and/or its prodrugs together with at least one other active ingredient effective in the treatment or prophylaxis of osteoporosis or in the inhibition of bone resorption like those listed before, together with a customary pharmaceutically acceptable carrier. The above explanations on pharmaceutical compositions correspondingly apply to such pharmaceutical combination compositions.

Apart from use as inhibitors of bone resorption by osteoclasts, the compounds of the formula I and their physiologically tolerable salts and their prodrugs can be used, for example, as inhibitors of tumor growth and tumor metastasis, as antiinflammatories, for the therapy or prophylaxis of rheumatoid arthritis, for the therapy of psoriasis, for the therapy or prophylaxis of cardiovascular disorders such as arteriosclerosis or restenoses, for the therapy or prophylaxis of nephropathies or retinopathies such as, for example, diabetic retinopathy. As inhibitors of tumor growth or tumor metastasis the compounds of the formula I and/or their physiologically tolerable salts and/or their prodrugs can also favorably be used in combination with conventional cancer therapy. Examples of conventional cancer therapy are given in Bertino (Editor), Encyclopedia of Cancer, Academic Press, 1997 which is incorporated herein by reference. All the above statements relating to the use of the compounds of formula I in combination with conventional osteoporosis therapy like, for example, possible modes of administration and pharmaceutical combination compositions, correspondingly apply to the use of the compounds of formula I in combination with conventional cancer therapy.

When using the compounds of the formula I, the dose can vary within wide limits and, as is customary, is to be suited to the individual conditions in each individual case. It depends, for example, on the compound employed, on the nature and severity of the disease to be treated, or on whether an acute or chronic condition is treated or whether prophylaxis is carried out. In the case of oral administration, the daily dose is in general from about 0.01 to about 100 mg/kg, preferably from about 0.1 to about 50 mg/kg, in particular from about 0.1 to about 5 mg/kg, to achieve effective results in an adult weighing about 75 kg (in each case in mg per kg of body weight). Also in the case of intravenous administration the daily dose is in general from about 0.01 to about 100 mg/kg, preferably from about 0.05 to about 10 mg/kg (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Apart from use as pharmaceutical active ingredients, the compounds of formula I can also be used as vehicles or carriers of other active ingredients in order to transport the active ingredient specifically to the site of action (=drug targeting; see, for example, Targeted Drug Delivery, R. C. Juliano, Handbook of Experimental Pharmacology, Vol. 100, Ed. Born, G. V. R. et al., Springer Verlag which is incorporated herein by reference). The active ingredients to be transported are in particular those which can be used for the treatment of the abovementioned diseases.

The compounds of the formula I and their salts can furthermore be employed for diagnostic purposes, for example in in vitro diagnoses, and as auxiliaries in biochemical investigations in which blocking of the vitronectin receptor or influencing of cell-cell or cell-matrix interactions is desired. They can furthermore be used as synthesis intermediates for the preparation of other compounds, in particular of other pharmaceutical active ingredients, which are obtainable from the compounds of the formula I, for example by introduction of substituents or modification of functional groups.

EXAMPLES

Example 1

(2S)-2-Benzyloxycarbonylamino-3-(6-(4-(5,6,7,8-tetrahydro-[1,8]naphthyridin-2-yl)-piperidin-1-yl)-purin-9-yl)-propionic acid

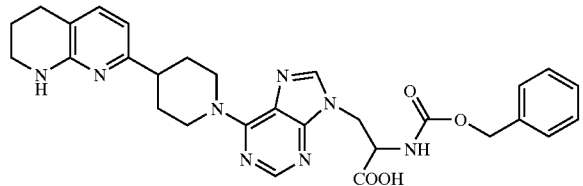

a) 4-([1,8]Naphthyridin-2-yl)-piperidine-1-carboxylic acid tert-butyl ester 3.14 g of 1-tert-butoxycarbonyl-4-acetyl-piperidine and 1.83 g of 2-amino-3-formyl-pyridine were refluxed with 0.25 g of L-proline in n-butanol for 72 hours. After removing the solvent in vacuo the residue was combined with the residue obtained in an identical reaction and chromatographed on silica gel with ethyl acetate/n-heptane (1:1) to give 1.08 g of the title compound.

b) 4-(5,6,7,8-Tetrahydro-[1,8]naphthyridin-2-yl)-piperidine-1-carboxylic acid tert-butyl ester 0.52 g of the compound of step a) were dissolved in 25 ml of ethyl acetate, and 0.11 g of 10% palladium on charcoal were added under an inert gas atmosphere. Hydrogenation was performed with this mixture under stirring at ambient temperature until thin layer chromatography did no more show the starting material. The catalyst was removed carefully and washed twice with ethyl acetate. The combined solutions were filtered again and the solvents removed in vacuo. Yield: 0.46 g.

c) 7-(Piperidin-4-yl)-1,2,3,4-tetrahydro-[1,8]naphthyridine 0.157 g of the compound of step b) were dissolved in 5 ml of methylene chloride, and 1 ml of trifluoroacetic acid was added under stirring. Stirring was continued for 2.5 hours at room temperature. After removal of the solvents in vacuo the oily residue was triturated with diethyl ether. Yield: 0.145 g of a colourless amorphous solid.

d) (2S)-2-Benzyloxycarbonylamino-3-(6-(4-(5,6,7,8-tetrahydro-[1,8]naphthyridin-2-yl)-piperidin-1-yl)-purin-9-yl)-propionic acid tert-butyl ester 0.44 g of the compound of step c) were dissolved in 5 ml of anhydrous dimethylformamide. 0.7 ml of N,N-diisopropylethylamine were added together with 0.58 g of (S)-2-benzyloxycarbonylamino-3-(6-chloro-purin-9-yl)-propionic acid tert-butyl ester, and the mixture was stirred at ambient temperature overnight. Thin layer chromatographic control exhibited only incomplete reaction. Stirring was therefore continued for 6 hours at 40° C. until the reaction was complete. The solvent was removed in vacuo and the residue was dissolved in dichloromethane and washed twice with water. The organic phase was dried with anhydrous magnesium sulfate and, after filtration, concentrated in vacuo. The raw material was chromatographed on silica gel with ethyl acetate and ethyl acetate/methanol (1:10). Yield: 224 mg.

The (2S )-2-benzyloxycarbonylamino-3-(6-chloro-purin-9-yl)-propionic acid tert-butyl ester can be prepared from 6-chloropurine and N-benzyloxycarbonyl-L-serine tert-butyl ester in the presence of triphenylphosphine and diethyl azodicarboxylate according to the procedure described in EP-A-853084 which is incorporated herein by reference.

e) (2S)-2-Benzyloxycarbonylamino-3-(6-(4-(5,6,7,8-tetrahydro-[1,8]naphthyridin-2-yl)-piperidin-1-yl)-purin-9-yl)-propionic acid 219 mg of the compound of step d) were dissolved in 12 ml of dichloromethane and 2 ml trifluoroacetic acid were added under stirring at ambient temperature. After 6 hours the reaction was complete. The solvents were removed in vacuo. The residue was mixed with toluene and this mixture was again evaporated. The resulting resin was triturated with diethylether. After filtration 210 mg of a faint yellow solid were isolated. MS (ES$^+$): m/e=557.2 (M+H)$^+$.

Example 2

(2S)-2-Benzenesulfonylamino-3-(6-(4-(5,6,7,8-tetrahydro-[1,8]naphthyridin-2-yl)-piperidin-1-yl)-purin-9-yl)-propionic acid

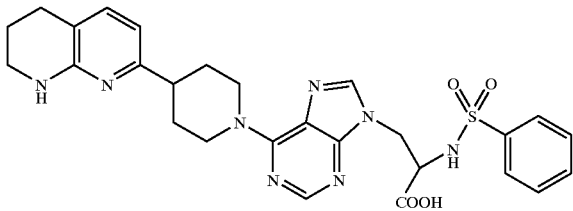

a) (2S)-2-Amino-3-(6-(4-(5,6,7,8-tetrahydro-[1,8]naphthyridin-2-yl)-piperidin-1-yl)purin-9-yl)-propionic acid tert-butyl ester 878 mg of the compound of example 1, step d) were dissolved in 50 ml of methanol and 0.4 ml of acetic acid. Under a nitrogen atmosphere 350 mg of 10% palladium on charcoal were carefully added, and hydrogenation was performed under shaking of the reaction vessel. After 5 hours the reaction was complete. The solvents were removed after filtration of the catalyst Yield: 680 mg of a resinous product. MS (ES$^+$): m/e=479.3 (M+H)$^+$.

b) (2S)-2-Benzenesulfonylamino-3-(6-(4-(5,6,7,8-tetrahydro-[1,8]naphthyridin-2-yl)-piperidin-1-yl)-purin-9-yl)-propionic acid tert-butyl ester 135 mg of the compound of step a) were dissolved in 2.2 ml of dimethylformamide and a solution of 44.2 mg of benzenesulfonyl chloride in 1.5 ml of dimethylformamide was added. After stirring overnight, the reaction was complete. The solvent was removed in vacuo, the residue was dissolved in dichloromethane and washed with water, a 10% aqueous solution of sodium bicarbonate and again with water. After drying of the organic phase with anhydrous magnesium sulfate and filtration the solvent was removed in vacuo and the residue was chromatographed on silica gel with ethyl acetate. The fractions containing the title compound were pooled and evaporated. Yield: 38 mg. MS (ES$^+$): m/e=619.2 (M+H)$^+$.

c) (2S)-2-Benzenesulfonylamino-3-(6-(4-(5,6,7,8-tetrahydro-[1,8]naphthyridin-2-yl)-piperidin-1-yl)-purin9-yl)-propionic acid 38 mg of the compound of step b) were dissolved in 1.5 ml of dichloromethane, and 1.5 ml of trifluoroacetic acid were added. After stirring for 5 hours at ambient temperature additional 0.1 ml of trifluoroacetic acid were added and stirring was continued for further 1.5 hours. The solvents were removed in vacuo, the residue was dissolved in acetic acid and again the solvent was removed in vacuo. The remaining resin was triturated with diethylether and the product isolated by filtration. Yield: 29 mg. MS (ES$^+$): m/e=563.1 (M+H)$^+$.

Analogously to the procedure described in example 2 the compounds of examples 3 to 6 were prepared.

Example 3

(2S)-2-(4-Chlorobenzenesulfonylamino)-3-(6-(4-(5,6,7,8-tetrahydro-[1,8]naphthyridin-2-yl)-piperidin-1-yl)-purin-9-yl)-propionic acid

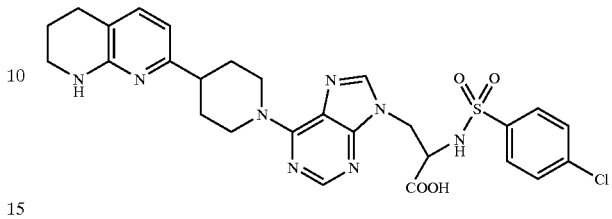

From 135 mg of the compound of example 2, step a) and 52.8 mg of 4-chlorobenzenesulfonyl chloride 45 mg of the title compound were obtained. MS (ES$^+$): m/e=597.1 and 599.1 (M+H)$^+$.

Example 4

(2S)-2-(Naphthalene-1-sulfonylamino)-3-(6-(4-(5,6,7,8-tetrahydro-[1,8]naphthyridin-2-yl)-piperidin-1-yl)-purin-9-yl)-propionic acid

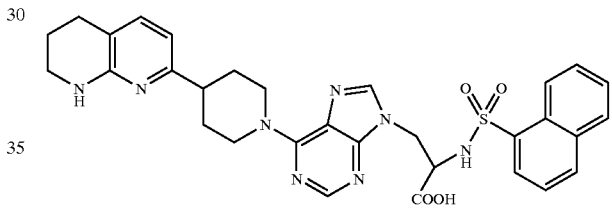

From 135 mg of the compound of example 2, step a) and 56.7 mg of naphthalene-1-sulfonyl chloride 74 mg of the title compound were obtained. MS (ES$^+$): m/e=613.1 (M+H)$^+$.

Example 5

(2S)-3-(6-(4-(5,6,7,8-Tetrahydro-[1,8]naphthyridin-2-yl)-piperidin-1-yl)-purin-9-yl)-2-(4-trifluoromethylbenzenesulfonylamino)-propionic acid

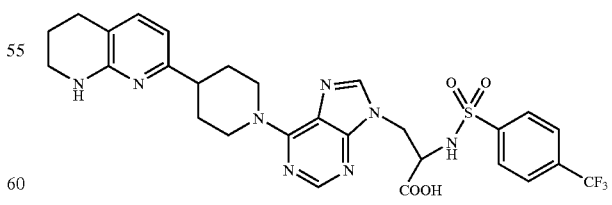

From 135 mg of the compound of example 2, step a) and 61.2 mg of 4-trifluoromethylbenzenesulfonyl chloride 11.4 mg of the title compound were obtained. MS (FAB): m/e=631.1 (M+H)$^+$.

Example 6

(2S)-2-(Butane-1-sulfonylamino)-3-(6-(4-(5,6,7,8-tetrahydro-[1,8]naphthyridin-2-yl)-piperidin-1-yl)-purin-9-yl)-propionic acid

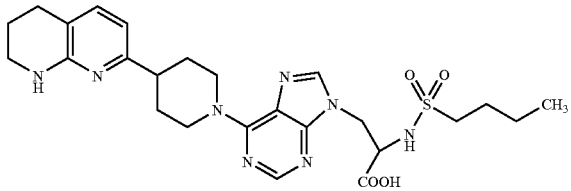

From 135 mg of the compound of example 2, step a) and 21 mg of butane-1-sulfonyl chloride 13 mg of the title compound were obtained. MS (ES+): m/e=543.2 (M+H)+.

Pharmacological Testing

1) Kistrin Binding Assay

The inhibition of the binding of kistrin to human vitronectin receptor (VnR) described below is a test method by which the antagonistic action of the compounds of the invention on the vitronectin receptor $\alpha_v\beta_3$ can be determined ($\alpha_v\beta_3$ ELISA Test; the test method is abbreviated as "K/VnR" in the listing of the test results).

Purification of Kistrin

Kistrin is purified according to the methods of Dennis et al., as described in Proc. Natl. Acad. Sci. USA 87 (1989) 2471 and Proteins: Structure, Function and Genetics 15 (1993) 312.

Purification of Human Vitronectin Receptor ($\alpha_v\beta_3$)

Human vitronectin receptor is obtained from the human placenta according to the method of Pytela et al., Methods Enzymol. 144 (1987) 475. Human vitronectin receptor $\alpha_v\beta_3$ can also be obtained from some cell lines (for example from 293 cells, a human embryonic kidney cell line) which are co-transfected with DNA sequences for both subunits $\alpha_v$ and $\beta_3$ of the vitronectin receptor. The subunits are extracted with octyl glycoside and then chromatographed through concanavalin A, heparin-Sepharose and S-300.

Monoclonal Antibodies

Murine monoclonal antibodies which are specific for the $\beta_3$ subunits of the vitronectin receptor, are prepared according to the method of Newman et al., Blood, 1985, 227, or by a similar process. The rabbit Fab 2 anti-mouse Fc conjugate to horseradish peroxidase (anti-mouse Fc HRP) was obtained from Pel Freeze (Catalog No. 715 305-1).

ELISA Test

The ability of substances to inhibit the binding of kistrin to the vitronectin receptor can be determined using an ELISA test. For this purpose, Nunc 96-well microtiter plates are coated with a solution of kistrin (0.002 mg/ml) according to the method of Dennis et al., as described in Proteins: Structure, Function and Genetics 15 (1993) 312. The plates are then washed twice with PBS/0.05% Tween-20 and blocked by incubating (60 min) with bovine serum albumin (BSA, 0.5%, RIA grade or better) in buffer solution (Tris-HCl (50 mM), NaCl (100 mM), MgCl$_2$ (1 mM), CaCl$_2$ (1 mM), MnCl$_2$ (1 mM), pH 7). Solutions of known inhibitors and of the test substances are prepared in concentrations from $2\times10^{-12}$ to $2\times10^{-6}$ mol/l in assay buffer (BSA (0.5%, RIA grade or better); Tris-HCl (50 mM); NaCl (100 mM), MgCl$_2$ (1 mM), CaCl$_2$ (1 mM), MnCl$_2$ (1 mM), pH 7). The blocked plates are emptied, and in each case 0.025 ml of this solution which contains a defined concentration ($2\times10^{-12}$ to $2\times10^{-6}$ mol/l) either of a known inhibitor or of a test substance, are added to each well. 0.025 ml of a solution of the vitronectin receptor in assay buffer (0.03 mg/ml) is pipetted into each well of the plate and the plate is incubated at room temperature for 60–180 min on a shaker. In the meantime, a solution (6 ml/plate) of a murine monoclonal antibody specific for the $\beta_3$ subunit of the vitronectin receptor is prepared in assay buffer (0.0015 mg/ml). A second rabbit antibody (0.001 ml of stock solution/6 ml of the murine monoclonal anti-$\beta_3$ antibody solution) which is an anti-mouse Fc HRP antibody conjugate is added to this solution, and this mixture of murine anti-$\beta_3$ antibody and rabbit anti-mouse Fc HRP antibody conjugate is incubated during the time of the receptor-inhibitor incubation. The test plates are washed four times with PBS solution which contains 0.05% Tween-20, and in each case 0.05 ml/well of the antibody mixture is pipetted into each well of the plate and incubated for 60–180 min. The plate is washed four times with PBS/0.05% Tween-20 and then developed with 0.05 ml/well of a PBS solution which contains 0.67 mg/ml of o-phenylenediamine and 0.012% of H$_2$O$_2$. Alternatively to this, o-phenylenediamine can be employed in a buffer (pH 5) which contains Na$_3$PO$_4$ and citric acid. The color development is stopped using 1 N H$_2$SO$_4$ (0.05 ml/well). The absorption for each well is measured at 492–405 nm and the data are evaluated by standard methods.

2) Vitronectin/293 Cell Test

In this test the inhibition of binding of 293 cells to human vitronectin (Vn) by the compounds of the invention is determined (the test method is abbreviated as Vn/293 cell test in the listing of the test results).

Purification of Human Vitronectin

Human vitronectin was isolated from human plasma and purified by affinity chromatography according to the method of Yatohgo et al., Cell Structure and Function 23 (1988) 281.

Cell Test 293 cells, a human embryonic kidney cell line, which were cotransfected with DNA sequences for the $\alpha_v$ and $\beta_3$ subunits of the vitronectin receptor $\alpha_v\beta_3$, were selected for a high rate of expression (>500,000 $\alpha_v\beta_3$ receptors/cell) according to the FACS method. The selected cells were cultured and sorted again by means of FACS in order to obtain a stable cell line (15 D) with expression rates >1,000,000 copies of $\alpha_v\beta_3$ per cell.

A Linbro 96-well tissue culture plate with a flat bottom was coated overnight at 4° C. with human vitronectin (0.01 mg/ml, 0.05 ml/well) in phosphate-buffered saline solution (PBS) and then blocked with 0.5% strength BSA (bovine serum albumin). Solutions of the test substances from $10^{-10}$ mol/l to $2\times10^{-3}$ mol/l in glucose-containing DMEM medium were prepared and 0.05 ml/well of the solution were added to the plate in each case. The cells which expressed high levels of $\alpha_v\beta_3$ (for example 15 D) were suspended in glucose-containing DMEM medium and the suspension was adjusted to a content of 25,000 cells/0.05 ml of medium. 0.05 ml of this cell suspension was added to each well and the plate was incubated at 37° C. for 90 min. The plate was washed 3 times with warm PBS in order to remove unbound cells. The bound cells were lyzed in citrate buffer (25 mM, pH 5.0) which contained 0.25% Triton X-100. The hexoseamidase substrate p-nitrophenyl-N-acetyl-β-D-glucosaminide was then added and the plate was incubated at 37° C. for 90 min. The reaction was stopped with a glycine (50 mM)/EDTA (5 mM) buffer (pH 10.4) and the absorption of each well was measured at 405 to 650 nm. The data were analyzed according to standard methods.

3) Pit Assay

The inhibition of bone resorption by the compounds of the invention can be determined, for example, with the aid of an osteoclast resorption test ("Pit Assay"), for example analogously to WO-A-95/32710 which is incorporated herein by reference.

The following test results (inhibitory concentrations $IC_{50}$) were obtained.

| Compound | K/VnR $IC_{50}$ (nM) | Vn/293 cell test $IC_{50}$ (nM) | Pit Assay $IC_{50}$ (nM) |
| --- | --- | --- | --- |
| Example 1 | 10 | 78 | |
| Example 2 | 4.8 | 23 | |
| Example 3 | 5.1 | 15 | 0.3 |
| Example 4 | 6.4 | 24 | <10 |
| Example 5 | 5 | 22 | |
| Example 6 | 18 | 115 | |

What is claimed is:
1. A compound selected from the group consisting of a compound of the formula

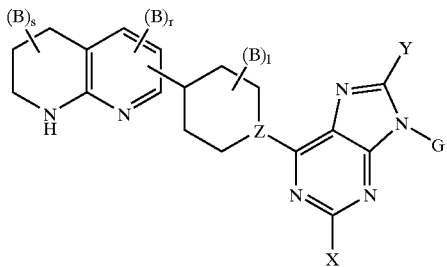

I in which
G is

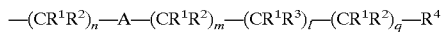

—$(CR^1R^2)_n$—A—$(CR^1R^2)_m$—$(CR^1R^3)_r$—$(CR^1R^2)_q$—$R^4$

A is selected from the group consisting of a direct bond, —C(O)$NR^5$—, —$NR^5$—C(O)—, —C(O)—, —$NR^5$—, —O—, —S—, —S(O)—, —S(O)$_2$—, ($C_2$–$C_4$)-alkynediyl, ($C_2$–$C_4$)-alkenediyl and ($C_5$–$C_{14}$)-arylene wherein the arylene residue one, two, three, four or five ring carbon atoms can be replaced by a heteroatom selected from the group consisting of nitrogen, oxygen and sulfur, or a divalent residue of a 3-membered to 7-membered saturated or unsaturated ring which can contain one or two ring heteroatoms selected from the group consisting of nitrogen, sulfur and oxygen and which can be monosubstituted or disubstituted by a member selected from the group consisting of =O, =S and $R^3$, B are individually selected from the group consisting of ($C_1$–$C_{18}$)-alkyl, ($C_3$–$C_{14}$)-cycloalkyl, ($C_3$–$C_{14}$)-cycloalkyl-($C_1$–$C_8$)-alkyl-, ($C_5$–$C_{14}$)-($C_5$–$C_{14}$)-aryl-($C_1$–$C_8$)-alkyl-, ($C_5$–$C_{14}$)-heteroaryl, ($C_5$–$C_{14}$)-heteroaryl-($C_1$–$C_8$)-alkyl-, fluorine, chlorine, bromine, hydroxy, cyano, trifluoromethyl, nitro, hydroxycarbonyl-, ($C_1$–$C_6$)-alkoxy, ($C_1$–$C_6$)-alkoxy-($C_1$–$C_6$)-alkyl-, ($C_1$–$C_6$)-alkoxycarbonyl-, ($C_1$–$C_6$)-alkylcarbonyl-, $C_5$–$C_{14}$)-arylcarbonyl-, ($C_1$–$C_6$)-alkylamino-carbonyl-, ($C_1$–$C_6$)-alkoxy-($C_1$–$C_6$)-alkoxy-, ($C_5$–$C_{14}$)-aryl-($C_1$–$C_8$)-alkylcarbonyl-, ($C_1$–$C_6$)-alkanoylamino-, ($C_1$–$C_6$)-alkylsulfonyolamino-, ($C_5$–$C_{14}$)-arylsulfonylamino-, ($C_1$–$C_6$)-alkylamino-, di-(($C_1$–$C_6$)-alkyl)amino-, ($C_1$–$C_6$)-alkylsulfonyl-, aminosulfonyl-, ($C_5$–$C_{14}$)-arylsulfonyl-, ($C_5$–$C_{14}$)-aryl-($C_1$–$C_8$)-alkylsulfonyl-, ($C_5$–$C_{14}$)-aryl and ($C_5$–$C_{14}$)-heteroaryl;

X is selected from the group consisting of hydrogen, $NR^6R^{6+}$, fluorine, chlorine, bromine, —$OR^6$, —$SR^6$, hydroxy-($C_1$–$C_6$)-alkyl-NH—, (hydroxy-($C_1$–$C_6$)-alkyl)$_2$N—, amino-($C_1$–$C_6$)-alkyl-NH—, (amino-($C_1$–$C_6$)-alkyl)$_2$N—, hydroxy-($C_1$–$C_6$)-alkyl-O—, hydroxy-($C_1$–$C_6$)-alkyl-S— and —NH—C(O)—$R^6$);

Y is selected from the group consisting of $R^6$, fluorine, chlorine, bromine, cyano, —$NR^6R^{6+}$—, —$OR^6$, —$SR^6$ and hydroxy-($C_1$–$C_6$)-alkyl-NH;

Z is N or —CH:

$R^1$ and $R^2$ are individually selected from the group consisting of hydrogen, fluorine, chlorine, cyano, nitro, ($C_1$–$C_{10}$)-alkyl, ($C_3$–$C_{14}$)-cycloalkyl, ($C_3$–$C_{14}$)-cycloalkyl-($C_1$–$C_8$)-alkyl-, ($C_5$–$C_{14}$)-aryl, ($C_5$–$C_{14}$)-aryl-($C_1$–$C_8$)-alkyl-, ($C_5$–$C_{14}$)-heteroaryl, ($C_5$–$C_{14}$)-heteroaryl-($C_1$–$C_8$)-alkyl-, $R^6$—O—$R^7$, $R^6$—S(O)$_p$—$R^7$, $R^6S(O)_2NHR^7$, $R^6OC(O)NHR^7$ and $R^6R^6N$—$R^7$;

$R^3$ is selected from the group consisting of hydrogen, fluorine, chlorine, cyano, nitro, ($C_1$–$C_{18}$)-alkyl, ($C_2$–$C_{18}$)-alkenyl, ($C_2$–$C_{18}$)-alkynyl, ($C_3$–$C_{14}$)-cycloalkyl, ($C_3$–$C_{14}$)-cycloalkyl-($C_1$–$C_8$)-alkyl-, ($C_5$–$C_{14}$)-aryl, ($C_5$–$C_{14}$)-aryl-($C_1$–$C_8$)-alkyl-, ($C_5$–$C_{14}$)-heteroaryl, ($C_5$–$C_{14}$)-heteroaryl-($C_1$–$C_8$)-alkyl-, $R^6$—O—$R^7$, $R^6R^{6+}R^7$, $R^6C(O)$—O—$R^7$, $R^6C(O)R^7$, $R^6OC(O)R^7$), ($R^6N(R^6)C(O)OR^7$, $R^6S(O)_pN(R^5)R^7$, $R^6OC(O)N(R^5)R^7$, $R^6C(O)N(R^5)R^7$, $R^6N(R^{6+})C(O)N(R^5)R^7$, $R^6N(R^{6+})S(O)_pN(R^5)R^7$, $R^6S(O)_pR^7$, $R^6SC(O)N(R^5)R^7$, $R^6N(R^{6+})C(O)R^7$ and $R^6N(R^{6+})S(O)_pR^7$, where alkyl, cycloalkyl, aryl, and heteroaryl can be monosubstituted or polysubstituted by a member selected from the group consisting of $R^6$, fluorine, chlorine, bromine, cyano, trifluoromethyl, $R^6R^{6+}NR^7$, nitro, $R^6OC(O)R^7$, $R^6C(O)R^7$, $R^6N(R^{6+})C(O)R^7$, $R^6N(R^{6+})S(O)_pR^7$ and $R^6$—O—$R^7$, and where the $R^3$S are independent of one another and can be identical or different;

$R^4$ is selected from the group consisting of —$C(O)R^8$, —$C(S)R^8$, —$S(O)_pR^8$, —$S(O)_pR^8$, —$P(O)R^8R^{8+}$ and a 4-membered to 8-membered saturated or unsaturated heterocycle which contains 1, 2, 3 or 4 heteroatoms selected from the group consisting of nitrogen, oxygen and sulfur;

$R^5$ is selected from the group consisting of hydrogen, ($C_1$–$C_{10}$)-alkyl, ($C_3$–$C_{14}$)-cycloalkyl-($C_1$–$C_8$)-alkyl-, ($C_5$–$C_{14}$)-aryl and ($C_5$–$C_{14}$)-aryl-($C_1$–$C_8$)-alkyl;

$R^6$ and $R^{6+}$ are individually selected from the group consisting of hydrogen, ($C_1$–$C_{18}$)-alkyl, ($C_3$–$C_{18}$)-alkyl, ($C_3$–$C_{14}$)-aryl, ($C_5$–$C_{14}$)-aryl-($C_1$–$C_8$)-alkyl-, $C_5$–$C_{14}$)-heteroaryl and ($C_5$–$C_{14}$)-heteroaryl-($C_1$–$C_8$)-alkyl- where aryl, heteroaryl, cycloalkyl and alkyl can be substituted one, two or three times by individual substituents selected from the group consisting of fluorine, chlorine, bromine, cyano, trifluoromethyl, nitro, hydroxycarbonyl-, ($C_1$–$C_6$)-alkyl, ($C_1$–$C_6$)- alkoxy, $(C_1-C_6)$-alkoxy-$(C_1-C_6)$-alkyl-, $(C_1-C_6)$-alkoxycarbonyl-, $(C_1-C_6)$-alkylcarbonyl-, $(C_1-C_6)$-alkylaminocarbonyl-, $(C_1-C_6)$-alkoxy-$(C_1-C_6)$-alkoxy-, $(C_5-C_{14})$-arylcarbonyl-, $(C_5-C_{14})$-aryl-$(C_1-C_8)$-alkylcarbonyl-, $(C_1-C_6)$-alkanoylamino-, $(C_5-C_{14})$-arylsulfonylamino-, $(C_1-C_6)$-alkylsulfonylamino-, $(C_1-C_6)$-alkylamino-, di($(C_1-C_6)$-alkyl)amino-, $(C_1-C_6)$-alkylsulfonyl, $(C_1-C_6)$-alkylaminosulfonyl-, $(C_5-C_{14})$-arylaminosulfonyl-, $(C_5-C_{14})$-aryl-$(C_1-C_8)$-alkylaminosulfonyl, $(C_5-C_{14})$-arylsulfonyl-, $(C_5-C_{14})$-aryl-$(C_1-C_8)$-alkylsulfonyl, $(C_5-C_{14})$-aryl and $(C_5-C_{14})$-heteroaryl;

$R^7$ is $(C_1-C_4)$-alkanediyl or a direct bond, where all $R^7$ are independent of one another and can be identical or different;

$R^8$ and $R^{8+}$ are individually selected from the group consisting of hydroxy, $(C_1-C_8)$-alkoxy, $(C_5-C_{14})$-aryl-$(C_1-C_4)$-alkoxy-, $(C_5-C_{14})$-aryloxy, $(C_1-C_8)$-alkylcarbonyloxy-$(C_1-C_4)$-alkoxy-, $(C_5-C_{14})$-aryl-$(C_1-C_8)$-alkylcarbonyloxy-$(C_1-C_8)$-alkoxy-, $NR^6R^6$, (di-(($C_1-C_8$)-alkyl)amino)carbonylmethyloxy-, (di(($C_5-C_{14}$)-aryl-$(C_1-C_8)$-alkyl)amino)carbonylmethyloxy-, $(C_5-C_{14})$-arylamino-, an amino acid, $N$—(($C_1-C_4$)-alkylpiperidin-4-yloxy-, 2-methylsulfonylethoxy-, 1,3-thiazol-2-ylmethyloxy-, 3-pyridylmethyloxy-, 2-(di-(($C_1-C_4$)-alkyl)amino)-ethoxy and $Q^-(CH_3)_3N^+$—$CH_2$—$CH_2$—$O$— in which $Q^-$ is a physiologically tolerable anion;

n is zero, one, two, three, four or five;
m is zero, one, two, three, four or five:
i is zero or one;
q is zero, one or two;
r is zero, one or two;
s is zero, one, two or three;
t is zero, one, two, three, four, five, six, seven or eight;
p is zero, one or two, where all numbers p are independent of one another and can be identical or different;

in all their stereoisomeric forms and mixtures thereof in all ratios, and their non-toxic, physiologically tolerable salts.

2. A compound of claim 1, wherein G is

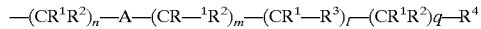

A is selected from the group consisting of a direct bond, —C(O)NR$^5$—, —NR$^5$C(O)—, —C(O)—, —NR$^5$—, —O—, —S—, —S(O)$_2$—, $(C_2-C_4)$-alkenediyl, $(C_2-C_4)$-alkenediyl, $(C_5-C_{14})$-arylene where in the arylene residue one, two, three, four or five ring carbon atoms can be replaced by a heteroatom selected from the group consisting of nitrogen, oxygen and sulfur, and a divalent residue of a 3-membered to 7-membered saturated or unsaturated ring which can contain one or two ring heteroatoms selected from the group consisting of nitrogen, sulfur and oxygen and which can be monosubstituted or disubstituted by a member selected from the group consisting of =O, =S and $R^3$;

B is selected from the group consisting of $(C_1-C_{12})$-alkyl, $(C_3-C_{14})$-cycloalkyl, $(C_3-C_{14})$-cycloalkyl-$(C_1-C_8)$-alkyl-, $(C_5-C_{14})$-aryl, $(C_5-C_{14})$-aryl-$(C_1-C_8)$-alkyl-, $(C_5-C_{14})$-heteroaryl, $(C_5-C_{14})$-heteroaryl-$(C_1-C_8)$-alkyl-, fluorine, chlorine, bromine, hydroxy, cyano, trifluoromethyl, nitro, hydroxycarbonyl-, $(C_1-C_6)$-alkoxy, $(C_1-C_6)$-alkoxy-$(C_1-C_6)$-alkyl, $(C_1-C_6)$-alkylcarbonyl-, $(_5-C_{14})$-arylcarbonyl-, $(_5-C_{14})$-aryl-$(_1-C_8)$-alkylcarbonyl-, $(C_1-C_6)$-alkylaminocarbonyl-, $(C_1-C_6)$-alkanoylamino-, $(C_1-C_6)$-alkylsulfonylamino-, $(C_5-C_{14})$-aryl-sulfonylamino-, $(C_1-C_{14})$-alkylamino-, di(($C_1-C_6$)-alkyl)amino-, $(C_1-C_6)$-alkylsulfonyl-, $(C_5-C_{14})$-arylsulfonyl-, $(C_5-C_{14})$-aryl-$(C_1-C_8)$-alkylsulfonyl-, $(C_5-C_{14})$-aryl and $(C_5-C_{14})$-heteroaryl, where all Bs are independent of one another and can be identical or different;

X is selected from the group consisting of hydrogen, $NH_2$, —NH—C(O)—$R^6$ and OH;

Y is hydrogen,

Z is N;

$R^1$ and $R^2$ are individually selected from the group consisting of hydrogen, fluorine, chlorine, cyano, nitro, $(C_1-C_{10})$-alkyl, $(C_3-C_{14})$-cycloalkyl, $(C_3-C_{14}$-)-cycloalkyl-$(C_1-C_8)$-alkyl-, $(C_5-C_{14})$-aryl, $(C_5-C_{14})$-aryl-$(C_1-C_8)$-alkyl-, $(C_5-C_{14})$-heteroaryl, $(C_5-C_{14})$-heteroaryl-$(C_1-C_8)$-alkyl-, $R^6$—O—$R^7$, $R^6$—S(O)$_p$—$R^7$, $R^6S(O)_2NHR^7$, $R^6OC(O)NHR^7$ and $R^6R^{6+}N$—$R^7$;

$R^3$ is selected from the group consisting of hydrogen, fluorine, chlorine, cyano, nitro, $(C_1-C_{18})$-alkyl, $(C_2-C_{18})$-alkenyl, $(C_2-C_{18})$-alkynyl, $(C_3-C_{14})$-cycloalkyl, $(C_3-C_{14})$-cycloalkyl-$(C_1-C_8$-alkyl-, $(C_5-C_{14})$-aryl, $(C_5-C_{14})$-aryl-$(C_1-C_8)$-alkyl-, $(C_5-C_{14})$-heteroaryl, $(C_5-C_{14})$-heteroaryl-$(C_1-C_8)$-alkyl-, $R^6$—O—$R^7$, $R^6R^{6+}R^7$, $R^6C(O)$—O—$R^7$, $R^6C(O)R^7$, $R^6OC(O)R^7$), ($R^6N(R^6)C(O)OR^7$, $R^6S(O)_pN(R^5)R^7$, $R^6OC(O)N(R^5)R^7$, $R^6C(O)N(R^5)R^7$, $R^6N(R^{6+})C(O)N(R^5)R^7$, $R^6N(R^{6+})S(O)_pN(R^5)R^7$, $R^6S(O)_pR^7$, $R^6SC(O)N(R^5)R^7$, $R^6N(R^{6+})C(O)R^7$ and $R^6N(R^{6+})S(O)_pR^7$, where alkyl, cycloalkyl, aryl, and heteroaryl can be monosubstituted or polysubstituted by a member selected from the group consisting of $R^6$, fluorine, chlorine, bromine, cyano, trifluoromethyl, $R^6R^{6+}NR^7$, nitro, $R^6OC(O)R^7$, $R^6C(O)R^7$, $R^6N(R^{6+})C(O)R^7$, $R^6N(R^{6+})S(O)_pR^7$ and $R^6$—O—$R^7$, and where $R^3S$ are independent of one another and can be identical or different;

and where all $R^3$ are independent of one another and can be identical or different;

$R^4$ is selected from the group consisting of —C(O)R$^8$, —C(S)R$^8$, —S(O)$_p$R$^8$, —S(O)$_p$R$^8$;

$R^5$ is selected from the group consisting of hydrogen, $(C_1-C_{10})$-alkyl, $(C_3-C_{14})$-cycloalkyl-$(C_1-C_8)$-alkyl- and $(C_5-C_{14})$-aryl-$(C_1-C_8)$-alkyl-, where all $R^5$ are independent of one another and can be identical or different;

$R^6$ and $R^{6+}$ are individually selected from the group consisting of hydrogen, $(C_1-C_{18})$-alkyl, $(C_3-C_{18})$-alkyl, $(C_3-C_{14})$-aryl, $(C_5-C_{14})$-aryl-$(C_1-C_8)$-alkyl-, $(C_5-C_{14})$-heteroaryl and $(C_5-C_{14})$-heteroaryl-$(C_1-C_8)$-alkyl- where aryl, heteroaryl, cycloalkyl and alkyl can be substituted one, two or three times by individual substituents selected from the group consisting of fluorine, chlorine, bromine, cyano, trifluoromethyl, nitro, hydroxycarbonyl-, $(C_1-C_6)$-alkyl, $(C_1-C_6)$-alkoxyl, $(C_1-C_6)$-alkoxy-$(C_1-C_6)$-alkyl-, $(C_1-C_6)$-alkoxycarbonyl-, $(C_1-C_6)$-alkylcarbonyl-, $(C_1-C_6)$-alkylaminocarbonyl-, $(C_1-C_6)$-alkoxy-$(C_1-C_6)$-alkoxy-, $(C_5-C_{14})$-arylcarbonyl-, $(C_5-C_{14})$-aryl-$(C_1-C_8)$-alkylcarbonyl-, $(C_1-C_6)$-alkanoylamino-, $(C_5-C_{14})$-arylsulfonylamino-, $(C_1-C_6)$-alkylsulfonylamino-, $(C_1-C_6)$-alkylamino-, di(($C_1-C_6$)-alkyl)amino-, $(C_1-C_6)$-alkylsulfonyl, $(C_1-C_6)$-alkylaminosulfonyl-, $(C_5-C_{14})$-arylaminosulfonyl-, $(C_5-C_{14})$-aryl-$(C_1-C_8)$-alkylaminosulfonyl, $(C_5-C_{14})$-arylsulfonyl-, $(C_5-C_{14})$-aryl-$(C_1-C_8)$-alkylsulfonyl, $(C_5-C_{14})$-aryl and $(C_5-C_{14})$-heteroaryl;

$R^7$ is $(C_1-C_4)$-alkanediyl or a direct bond, where all $R^7$ are independent of one another and can be identical or different;

$R^8$ and $R^{8+}$ are individually selected from the group consisting of hydroxy, $(C_1-C_8)$-alkoxy, $(C_5-C_{14})$-aryl-$(C_1-C_4)$-alkoxy-, $(C_5-C_{14})$-aryloxy, $(C_1-C_8)$-alkylcarbonyloxy-$(C_1-C_4)$-alkoxy-, $(C_5-C_{14})$-aryl-$(C_1-C_8)$-alkylcarbonyloxy-$(C_1-C_8)$-alkoxy-, $NR^6R^6$, (di-(($C_1-C_8$)-alkyl)amino)carbonylmethyloxy-, (di(($C_5-C_{14}$)-aryl-$(C_1-C_8)$-alkyl)amino)carbonylmethyloxy-, $(C_5-C_{14})$-arylamino-, an amino acid, N—(($C_1-C_4$)-alkylpiperidin-4-yloxy-, 2-methylsulfonylethoxy-, 1,3-thiazol-2-ylmethyloxy-, 3-pyridylmethyloxy-, 2-(di-(($C_1-C_4$)-alkyl)amino)-ethoxy and $Q^-(CH_3)_3$ $N^+$—$CH_2$—$CH_2$—O— in which $Q^-$ is a physiologically tolerable anion;

n is zero, one, two, three, four or five;

m is zero, one, two, three, four or five;

i is zero or one;

q is zero, one or two;

r is zero, one or two;

s is zero, one two or three;

t is zero, one, two, three, four, five, six, seven or eight;

p is zero, one or two, where all numbers p are independent of one another and can be identical or different;

in all their stereoisomeric forms and mixtures thereof in all ratios, and their non-toxic, physiologically tolerable salts.

3. A compound of claim 1, wherein G is

—$(CR^1R^2)_n$—A—$(CR—^1R^2)_m$—$(CR^1—R^3)_r$—$(CR^1R^2)_q$—$R^4$

A is selected from the group consisting of a direct bond, —C(O)NR^5—, —NR^5C(O)—, —C(O)—, —NR— and $(C_5-C_{14})$-arylene where in the arylene, one, two, three, four or five ring carbon atoms can be replaced by a heteroatom selected from the group consisting of nitrogen, oxygen and sulfur;

B is selected from the group consisting of $(C_1-C_6)$-alkyl, chlorine, hydroxy, cyano, trifluoromethyl, $(C_1-C_6)$-alkoxy, $(C_1-C_6)$-alkylcarbonyl-$(C_1-C_6)$-alkanoylamino-, $(C_1-C_6)$-alkylamino and di(($C_1-C_6$)-alkyl)-amino-, where all Bs are independent of one another and can be identical or different;

X is hydrogen;

Y is hydrogen;

Z is N;

$R^1$ and $R^2$ are individually selected from the group consisting of hydrogen, $(C_1-C_4)$-alkyl, $R^6S(O)$—$NHR^7$ and $R^6OC(O)NHR_7$;

$R^3$ is selected from the group consisting of hydrogen, $(C_1-C_{12})$-alkyl, $(C_2-C_{18})$-alkenyl, $(C_2-C_{18})$-alkynyl, $(C_3-C_{14})$-cycloalkyl, $(C_3-C_{14})$-cycloalkyl-$C_1-C_6)$-alkyl, $(C_5-C_{14})$-aryl-$(C_5-C_{14})$-aryl-$(C_1-C_8)$-alkyl-, $(C_5-C_{14})$-heteroaryl, $(C_5-C_{14})$-heteroaryl-$(C_1-C_6)$-alkyl-, $RR^6$—O—$R^7$, $R^6$—$S(O)_p$—$R^7$, $R^6S(O)_2NHR^7$, $R^6OC(O)NHR^7$ and $R^6R^{6+}N$—$R^7$;

$R^4$ is —$C(O)R^8$;

$R^5$ is hydrogen or $(C_1-C_4)$-alkyl, where are $R^5$s are independent of one another and can be identical or different;

$R^6$ and $R^{6+}$ are individually hydrogen, $(C_1-C_{12})$-alkyl, $(C_3-C_{14})$-cycloalkyl, $(C_3-C_{14})$-cycloalkyl-$(C_1-C_8)$-alkyl-, $(C_5-C_{14})$-aryl-, $(C_5-C_{14})$-aryl-$(C_1-C_8)$-alkyl-, $(C_5-C_{14}$-heteroaryl and $(C_5-C_{14})$-heteroaryl-$(C_1-C_8)$-alkyl- where aryl, heteroaryl, cycloalkyl and alkyl can be substituted one, two or three times by individual substituents selected from the group consisting of fluorine, chlorine, bromine, cyano, trifluoromethyl, nitro, hydroxycarbonyl-, $(C_1-C_6)$-alkyl, $(C_1-C_6)$-alkoxy, $(C_1-C_6)$-alkylamino-, di(($C_1-C_6$)-alkyl)amino-, $(C_5-C_{14})$-aryl and $(C_5-C_{14})$-heteroaryl, and where all $R^6$s and $R^{6+}$s are independent of one another and can be identical or different;

$R^7$ is $(C_1-C_2)$-alkanediyl or a direct bond, where all $R^7$s are independent of one another and can be identical or different;

$R^8$ is hydroxy or $(C_1-C_6)$-alkoxy, n is zero, one, two, three, four or five;

m is zero or one;

i is zero or one;

q is zero or one;

r is zero or one;

s is zero, one or two;

t is zero, one, two, three or four;

in all their stereoisomeric forms and mixtures thereof in all ratios, and their non-toxic physiologically tolerable salts.

4. A compound of claim 1, wherein G is

—$(CR^1R^2)_n$—A—$(CR—^1R^2)_m$—$(CR^1—R^3)_r$—$(CR^1R^2)_q$—$R^4$

A is a direct bond;

B is $(C_1-C_6)$-alkyl or hydroxy, where all Bs are independent of one another and can be identical or different;

X is hydrogen;

Y is hydrogen;

Z is n;

$R^1$ and $R^2$ are individually selected from the group consisting of hydrogen, $(C_1-C_4)$-alkyl, $R^6S(O)$—$NHR^7$ and $R^6OC(O)NHR_7$;

$R^3$ is selected from the group consisting of hydrogen, $(C_1-C_{12})$-alkyl, $(C_2-C_{18})$-alkenyl, $(C_2-C_{18})$-alkynyl, $(C_3-C_{14})$-cycloalkyl, $(C_3-C_{14})$-cycloalkyl-$(C_1-C_6)$-alkyl, $C_5-C_{14})$-aryl-$(C_5-C_{14})$-aryl-$(C_1-C_8)$-alkyl-, $(C_5-C_{14})$-heteroaryl, $(C_5-C_{14})$-heteroaryl-$(C_1-C_6)$-alkyl-, $R^6R^6N$—$R^7$, $R^6S(O)_pN(R^5)R^7$, $R^6OC(O)N(R^5)$ $R^7$, and $R^6C(O)N(R^5)R^7$, where alkyl, cycloalkyl, aryl, and heteroaryl can be monosubstituted or polysubstituted by a member selected from the group consisting of $R^6$, fluorine, chlorine, trifluoromethyl, $R^6C(O)R^7$ and $R^6$—O—$R^7$;

$R^4$ is —$C(O)R^8$;

$R^5$ is hydrogen or $(C_1-C_4)$-alkyl;

$R^6$ and $R^{6+}$ are individually hydrogen, $(C_1-C_{12})$-alkyl, $(C_3-C_{14})$-cycloalkyl, $(C_3-C_{14})$-cycloalkyl-$(C_1-C_8$-alkyl-, $(C_5-C_{14})$-aryl, $(C_5-C_{14})$-aryl-$(C_1-C_8)$-alkyl-, $(C_5-C_{14})$-heteroaryl or $(C_5-C_{14})$-heteroaryl-$(C_1-C_8)$-alkyl- where aryl, heteroaryl, cycloalkyl and alkyl can be substituted one, two or three times by at least one substituent selected from the group consisting of fluorine, chlorine, bromine, cyano, trifluoromethyl, $(C_1-C_6)$-alkyl, $(C_1-C_6)$-alkoxy, $(C_1-C_6)$-alkylamino-, di(($C_1-C_6$)-alkyl)amino-, $(C_5-C_{14})$-aryl and $(C_5-C_{14})$-heteroaryl, and where all $R^6$s and $R^{6+}$s are independent of one another and can be identical or different;

R$^7$ is a direct bond;
R$^8$ is hydroxy or (C$_1$–C4)-alkoxy;
n is zero, one or two;
m is zero or one;
i is zero or one;
q is zero or one;
r is zero or one;
s is zero, one or two;
t is zero;
in all their stereoisomeric forms and mixtures thereof in all ratios, and their nontoxic, physiologically tolerable salts.

5. A compound of claim 1 wherein G is

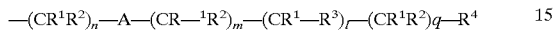

A is a direct bond;
X is hydrogen;
Z is N;
R$^1$ and R$^2$ are hydrogen or (C$_1$–C$_2$)-alkyl, where all R$^1$s and R$^2$s are independent of one another and can be identical or different;
R$^3$ is selected form the group consisting of R$^6$R$^{6+}$N—R$^7$, R$^6$S(O)$_2$N(R$^5$)R$^7$ and R$^6$C(O)N(R$^5$)R$^7$;
R$^4$ is —C(O)R$^8$;
R$^5$ is hydrogen or (C$_1$–C$_2$)-alkyl;
R$^6$ and R$^{6+}$ are individually selected from the group consisting of hydrogen, (C$_1$–C$_{12}$)-alkyl, (C$_1$–C$_{12}$)-alkyl, (C$_3$–C$_{14}$)-cycloalkyl, (C$_3$–C$_{14}$)-cycloalkyl-(C$_1$–C$_8$)-alkyl-, (C$_5$–C$_{14}$)-aryl-, (C$_5$–C$_{14}$)-aryl-(C$_1$–C$_8$)-alkyl-, (C$_5$–C$_{14}$)-aryl, (C$_5$–C$_{14}$)-aryl-(C$_1$–C$_8$)-alkyl, (C$_5$–C$_{14}$)-heteroaryl and (C$_5$–C$_{14}$)-heteroaryl-(C$_1$–C$_8$)-alkyl- where aryl, heteroaryl, cycloalkyl and alkyl can be substituted one, two or three times by at least one substituent selected from the group consisting of fluorine, chlorine, bromine, cyano, trifluoromethyl, (C$_1$–C$_6$)-alkyl, (C$_1$–C$_6$)-alkoxy, (C$_1$–C$_6$)-alkylamino-, di((C$_1$–C$_6$)-alkyl)amino-, (C$_5$–C$_{14}$)-aryl and (C$_5$–C$_{14}$)-heteroaryl, and where all R$^6$s and R$^{6+}$s are independent of one another and can be identical or different;
R$^7$ is a direct bond;
R$^8$ is hydroxy or (C$_1$–C$_4$)-alkoxy;
n is zero, one or two;
m is zero or one;
i is zero or one;
q is zero or one;
r is zero;
s is zero;
t is zero;
in all their stereoisomeric forms and mixtures thereof in all ratios, and their non-eoxic, physiologically tolerable salts.
6.

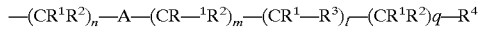

A is a direct bond;
X is hydrogen;
Z is N;
R$^1$ and R$^2$ are hydrogen;

R$^3$ is R$^6$S(O)$_2$N(R$^5$)R$^7$ and R$^6$C(O)N(R$^5$)R$^7$;
R$^4$ is —C(O)R$^8$;
R$^5$ is hydrogen;
R$^6$ is selected from the group consisting of (C$_1$–C$_{12}$)-alkyl, (C$_1$–C$_{12}$)-alkyl, (C$_3$–C$_{14}$)-cycloalkyl, (C$_3$–C$_{14}$)-)-aryl, (C$_5$–C$_{14}$)-aryl-(C$_1$–C$_8$)-alkyl-, (C$_5$–C$_{14}$)-heteroaryl and (C$_5$–C$_{14}$)-heteroaryl-(C$_1$–C$_8$)-alkyl- where aryl, heteroaryl, cycloalkyl and alkyl can be substituted one, two or three times by at least one substituent selected from the group consisting of fluorine, chlorine, bromine, cyano, trifluoromethyl, (C$_1$–C$_6$)-alkyl, (C$_1$–C$_6$)-alkoxy, (C$_1$–C$_6$)-alkylamino-, di((C$_1$–C$_6$)-alkyl)amino-, (C$_5$–C$_{14}$)-aryl and (C$_5$–C$_{14}$)-heteroaryl,
R$^7$ is a direct bond;
R$^8$ is hydroxy (C$_1$–C$_4$)-alkoxy;
n is one;
m is zero;
i is one;
q is zero;
r is zero;
s is zero;
t is zero;
in all their stereoisomeric forms and mixtures thereof in all ratios, and their non-toxic, physiologically tolerable salts.

7. A process for the preparation of a compound of claim 1 comprising reacting a compound of the formula VI

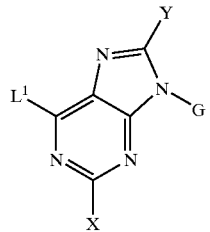

VI with a compound of the formula VIIa or of formula VIIb

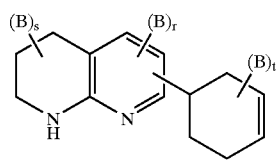

VIIb wherein L$^1$ is a cleaving group and B, G, X, Y, r, s and t are defined as in claim 1 but wherein functional groups can also be present in the form of precursor groups or in protected form.

8. A pharmaceutical composition, comprising an amount of a compound of claim 1 sufficient to treat osteoporosis and a pharmaceutically acceptable carrier.

9. A method of treating osteoporosis in warm-blooded animals comprising administering to warm-blooded animals in need thereof an amount of a compound of claim 1 sufficient to treat osteoporosis.

* * * * *